US012806265B2

(12) United States Patent
Yoneda et al.

(10) Patent No.: US 12,806,265 B2
(45) Date of Patent: Nov. 24, 2026

(54) RECOMBINANT MEASLES VIRUS

(71) Applicants: Misako Yoneda, Tokyo (JP); Chieko Kai, Tokyo (JP)

(72) Inventors: Misako Yoneda, Tokyo (JP); Chieko Kai, Tokyo (JP)

( * ) Notice: Subject to any disclaimer, the term of this patent is extended or adjusted under 35 U.S.C. 154(b) by 553 days.

(21) Appl. No.: 18/281,924

(22) PCT Filed: May 10, 2021

(86) PCT No.: PCT/JP2021/017632
§ 371 (c)(1),
(2) Date: Sep. 13, 2023

(87) PCT Pub. No.: WO2022/195900
PCT Pub. Date: Sep. 22, 2022

(65) Prior Publication Data

US 2024/0293533 A1 Sep. 5, 2024

(30) Foreign Application Priority Data

Mar. 15, 2021 (JP) ................................ 2021-041015

(51) Int. Cl.

| | |
|---|---|
| ***A61K 39/215*** | (2006.01) |
| ***A61P 37/04*** | (2006.01) |
| ***C07K 14/005*** | (2006.01) |
| ***C12N 15/86*** | (2006.01) |
| *A61K 39/00* | (2006.01) |

(52) U.S. Cl.
CPC ............ *A61K 39/215* (2013.01); *A61P 37/04* (2018.01); *C07K 14/005* (2013.01); *C12N 15/86* (2013.01); *A61K 2039/5256* (2013.01); *A61K 2039/58* (2013.01); *C12N 2760/18443* (2013.01); *C12N 2760/18452* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

| | | | | |
|---|---|---|---|---|
| 2012/0263751 A1* | 10/2012 | Kai | C07K 16/11 | 435/235.1 |
| 2013/0217757 A1* | 8/2013 | Lauer | A61K 31/7088 | 435/235.1 |
| 2023/0310581 A1* | 10/2023 | Li | A61K 39/215 | 424/221.1 |

FOREIGN PATENT DOCUMENTS

| | | |
|---|---|---|
| JP | 2010-099041 A | 5/2010 |
| JP | 2010-115154 A | 5/2010 |
| WO | 2004/000876 A1 | 12/2003 |

OTHER PUBLICATIONS

Horner et al. A highly immunogenic and effective measles virus-based Th1-biased COVID-19 vaccine. P.N.A.S. 2020, 117: 32657-32666.*

Yoneda et al. Recombinant Measles Virus Vaccine Expressing the Nipah Virus Glycoprotein Protects against Lethal Nipah Virus Challenge. PLoS One, 2013, 8(3): e58414.*

GenBank: MT409882.1. Synthetic construct nucleocapsid protein (N), phosphoprotein (P/V/C), V protein (P/V/C), C protein (P/V/C), matrix protein (M), fusion protein (F), hemagglutinin protein (H), and large protein (L) genes, complete cds. Dated May 11, 2020.*

Horner Cindy et al: "A highly immunogenic and effective measles virus-based Th1-biased COVID-19 vaccine", Proceedings of the National Academy of Sciences (PNAS), vol. 117, No. 51, Nov. 30, 2020 (Nov. 30, 2020), pp. 32657-32666, XP093236207, ISSN: 0027-8424, DOI: 10.1073/pnas.2014468117.

Yoneda M et al: "Recombinant Measles Virus Vaccine Expressing the Nipah Virus Glycoprotein Protects against Lethal Nipah Virus Challenge", Plos One, Public Library of Science, US, vol. 8, No. 3, Mar. 1, 2013 (Mar. 1, 2013), pp. e58414-1, XP002699590, ISSN: 1932-6203, DOI: 10.1371/JOURNAL.PONE.0058414 [retrieved on Mar. 14, 2013].

Database GenBank [Online] Oct. 26, 1995 (Oct. 26, 1995), "Measles virus (strain Edmonston B) RNA (infectious cDNA clone)", XP002812795, retrieved from GenBank accession No. Z66517.1 Database accession No. Z66517.

Search Report issued in EP Application No. 21931645.2, dated Jan. 28, 2025.

C. Kai et al., "Synthetic Construct Nucleocapsid Protein (N), Phosphoprotein (P/V/C), V Protein (P/V/C), C Protein (P/V/C), Matrix Protein (M), Fusion Protein (F), Hemagglutinin Protein (H), and Large Protein (L) Genes, Complete Cds", https://www.ncbi.nlm.nih.gov/nuccore/MT409882, May 11, 2020.

M. Lu et al., "A Safe and Highly Efficacious Measles Virus-Based 1-16 Vaccine Expressing SARS-CoV-2 Stabilized Prefusion Spike." PNAS, vol. 118, No. 12, pp. 1-23, 2021.

J.S. Rota et al., "Comparison of Sequences of the H, F, and N Coding Genes of Measles Virus Vaccine Strains1." Virus Research, vol. 31, pp. 317-330, 1994.

International Search Report,Int'l. Application No. PCT/JP2021/017632, mailed Jul. 13, 2021.

* cited by examiner

*Primary Examiner* — Nianxiang Zou
(74) *Attorney, Agent, or Firm* — Blank Rome LLP

(57) ABSTRACT

The present invention provides a recombinant measles virus useful as a live vaccine against COVID-19 and a vector used for production of the recombinant measles virus. That is, the present invention relates to a recombinant measles virus having a gene encoding a protein of the coronavirus SARS-COV-2 inserted between the N gene region and the P gene region in a measles virus genome; the recombinant measles virus in which the protein is a spike protein of SARS-COV-2 or a partial protein thereof; and a DNA in which a gene encoding a protein of SARS-COV-2 is inserted in a region ranging from the 1,686th base to the 1,694th base of a base sequence set forth in SEQ ID NO: 2.

10 Claims, 3 Drawing Sheets

Specification includes a Sequence Listing.

SEQUENCE LISTING

```
<160> NUMBER OF SEQ ID NOS: 4

<210> SEQ ID NO 1
<211> LENGTH: 15894
<212> TYPE: DNA
<213> ORGANISM: Artificial Sequence
<220> FEATURE:
<223> OTHER INFORMATION: Description of Artificial Sequence: Synthesized
      recombinant measles virus vector

<400> SEQUENCE: 1

accaaacaaa gttgggtaag gatagttcaa tcaatgatca tcttctagtg cacttaggat     60

tcaagatcct attatcaggg acaagagcag gattagggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtcaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540

gatggttcga gaacaaggaa atctcagata ttgaagtgca agaccctgag ggattcaaca    600

tgattctggg taccatccta gcccaaattt gggtcttgct cgcaaaggcg gttacggccc    660

cagacacggc agctgattcg gagctaagaa ggtggataaa gtacacccaa caaagaaggg    720

tagttggtga atttagattg gagagaaaat ggttggatgt ggtgaggaac aggattgccg    780

aggacctctc cttacgccga ttcatggtcg ctctaatcct ggatatcaag agaacacccg    840

gaaacaaacc caggattgct gaaatgatat gtgacattga tacatatatc gtagaggcag    900

gattagccag ttttatcctg actattaagt ttgggataga aactatgtat cctgctcttg    960

gactgcatga atttgctggt gagttatcca cacttgagtc cttgatgaac ctttaccagc   1020

aaatggggga aactgcaccc tacatggtaa tcctggagaa ctcaattcag aacaagttca   1080

gtgcaggatc ataccctctg ctctggagct atgccatggg agtaggagtg gaacttgaaa   1140

actccatggg aggtttgaac tttggccgat cttactttga tccagcatat tttagattag   1200
```

-continued

```
ggcaagagat ggtaaggagg tcagctggaa aggtcagttc cacattggca tctgaactcg   1260
gtatcactgc cgaggatgca aggcttgttt cagagattgc aatgcatact actgaggaca   1320
agatcagtag agcggttgga cccagacaag cccaagtatc atttctacac ggtgatcaaa   1380
gtgagaatga gctaccgaga ttggggggca aggaagatag gagggtcaaa cagagtcgag   1440
gagaagccag ggagagctac agagaaaccg ggcccagcag agcaagtgat gcgagagctg   1500
cccatcttcc aaccggcaca cccctagaca ttgacactgc atcggagtcc agccaagatc   1560
cgcaggacag tcgaaggtca gctgacgccc tgcttaggct gcaagccatg gcaggaatct   1620
cggaagaaca aggctcagac acggacaccc ctatagtgta caatgacaga aatcttctag   1680
actagggccg gcctgccgag gaccagaaca acatccgcct accctccatc attgttataa   1740
aaaacttagg aaccaggtcc acacagccgc cagcccatca accatccact cccacgattg   1800
gagcagatgg cagaagagca ggcacgccat gtcaaaaacg gactggaatg catccgggct   1860
ctcaaggccg agcccatcgg ctcactggcc atcgaggaag ctatggcagc atggtcagaa   1920
atatcagaca acccaggaca ggagcgagcc acctgcaggg aagagaaggc aggcagttcg   1980
ggtctcagca aaccatgcct ctcagcaatt ggatcaactg aaggcggtgc acctcgcatc   2040
cgcggtcagg gacctggaga gagcgatgac gacgctgaaa ctttgggaat ccccccaaga   2100
aatctccagg catcaagcac tgggctacag tgtcattatg tttatgatca cagcggtgaa   2160
gcggttaagg gaatccaaga tgctgactct atcatggttc aatcaggcct tgatggtgat   2220
agcaccctct caggaggaga caatgaatct gaaaacagcg atgtggatat tggcgaacct   2280
gataccgagg gatatgctat cactgaccgg ggatctgctc ccatctctat ggggttcagg   2340
gcttctgatg ttgaaactgc agaaggaggg gagatccacg agctcctgag actccaatcc   2400
agaggcaaca actttccgaa gcttgggaaa actctcaatg ttcctccgcc cccggacccc   2460
ggtagggcca gcacttccgg gacacccatt aaaaagggca cagacgcgag attagcctca   2520
tttggaacgg agatcgcgtc ttcattgaca ggtggtgcaa cccaatgtgc tcgaaagtca   2580
ccctcggaac catcagggcc aggtgcacct gcggggaacg tccccgagtg tgtgagcaat   2640
gccgcactga tacaggagtg gacacccgaa tctggcacca caatctcccc gagatcccag   2700
aataatgaag aagggggaga ccattatgat gatgagctgt tctctgatgt ccaagatatt   2760
aaaacagcct tggccaaaat acacgaggat aatcagaaga taatctccaa gctagaatca   2820
ctgctgttat tgaagggaga agttgagtca attaagaagc agatcaacag gcaaaatatc   2880
agcatatcca ccctggaagg acacctctca agcatcatga tcgccattcc tggacttggg   2940
aaggatccca acgaccccac tgcagatgtc gaaatcaatc ccgacttgaa acccatcata   3000
ggcagagatt caggccgagc actggccgaa gttctcaaga aacccgttgc cagccgacaa   3060
ctccaaggaa tgacaaatgg acggaccagt tccagaggac agctgctgaa ggaatttcag   3120
ctaaagccga tcgggaaaaa gatgagctca gccgtcgggt ttgttcctga caccggccct   3180
gcatcacgca gtgtaatccg ctccattata aaatccagcc ggctagagga ggatcggaag   3240
cgttacctga tgactctcct tgatgatatc aaaggagcca atgatcttgc caagttccac   3300
cagatgctgg tgaagataat aatgaagtag ctacagctca acttacctgc caaccccatg   3360
ccagtcgacc caactagtac aacctaaatc cattataaaa aacttaggag caaagtgatt   3420
gcctcccaag ttccacaatg acagagatct acgacttcga caagtcggca tgggacatca   3480
aagggtcgat cgctccgata caacccacca cctacagtga tggcaggctg gtgccccagg   3540
tcagagtcat agatcctggt ctaggcgaca ggaaggatga atgctttatg tacatgtttc   3600
```

```
tgctgggggt tgttgaggac agcgattccc tagggcctcc aatcgggcga gcatttgggt   3660
ccctgccctt aggtgttggc agatccacag caaagcccga aaaactcctc aaagaggcca   3720
ctgagcttga catagttgtt agacgtacag cagggctcaa tgaaaaactg gtgttctaca   3780
acaacacccc actaactctc ctcacacctt ggagaaaggt cctaacaaca gggagtgtct   3840
tcaacgcaaa ccaagtgtgc aatgcggtta atctgatacc gctcgatacc ccgcagaggt   3900
tccgtgttgt ttatatgagc atcacccgtc tttcggataa cgggtattac accgttcctg   3960
gaagaatgct ggaattcaga tcggtcaatg cagtggcctt caacctgctg gtgaccctta   4020
ggattgacaa ggcgataggc cctgggaaga tcatcgacaa tacagagcaa cttcctgagg   4080
caacatttat ggtccacatc gggaacttca ggagaaagaa gagtgaagtc tactctgccg   4140
attattgcaa aatgaaaatc gaaaagatgg gcctggtttt tgcacttggt gggatagggg   4200
gcaccagtct tcacattaga agcacaggca aaatgagcaa gactctccat gcacaactcg   4260
ggttcaagaa gaccttatgt tacccgctga tggatatcaa tgaagacctt aatcgattac   4320
tctggaggag cagatgcaag atagtaagaa tccaggcagt tttgcagcca tcagttcctc   4380
aagaattccg catttacgac gacgtgatca taaatgatga ccaaggacta ttcaaagttc   4440
tgtagaccgt agtgcccagc aatgcccgaa aacgaccccc ctcacaatga cagccagaag   4500
gcccggacaa aaaagccccc tccgaaagac tccacggacc aagcgagagg ccagccagca   4560
gccgacggca agcgcgaaca ccaggcggcc ccagcacaga acagccctga cacaaggcca   4620
ccaccagcca ccccaatctg catcctcctc gtgggacccc cgaggaccaa cccccaaggc   4680
tgcccccgat ccaaaccacc aaccgcatcc ccaccacccc cgggaaagaa acccccagca   4740
attggaaggc ccctccccct cttcctcaac acaagaactc cacaaccgaa ccgcacaagc   4800
gaccgaggtg acccaaccgc aggcatccga ctccctagac agatcctctc tccccggcaa   4860
actaaacaaa acttagggcc aaggaacata cacacccaac agaacccaga ccccggccca   4920
cggcgccgcg cccccaaccc ccgacaacca gagggagccc ccaaccaatc ccgccggctc   4980
ccccggtgcc cacaggcagg gacaccaacc cccgaacaga cccagcaccc aaccatcgac   5040
aatccaagac gggggggccc ccccaaaaaa aggcccccag gggccgacag ccagcaccgc   5100
gaggaagccc acccacccca cacacgacca cggcaaccaa accagaaccc agaccaccct   5160
gggccaccag ctcccagact cggccatcac cccgcagaaa ggaaaggcca caacccgcgc   5220
accccagccc cgatccggcg gggagccacc caacccgaac cagcacccaa gagcgatccc   5280
cgaaggaccc ccgaaccgca aaggacatca gtatcccaca gcctctccaa gtcccccggt   5340
ctcctcctct tctcgaaggg accaaaagat caatccacca cacccgacga cactcaactc   5400
cccaccccta aaggagacac cgggaatccc agaatcaaga ctcatccaat gtccatcatg   5460
ggtctcaagg tgaacgtctc tgccatattc atggcagtac tgttaactct ccaaacaccc   5520
accggtcaaa tccattgggg caatctctct aagatagggg tggtaggaat aggaagtgca   5580
agctacaaag ttatgactcg ttccagccat caatcattag tcataaaatt aatgcccaat   5640
ataactctcc tcaataactg cacgagggta gagattgcag aatacaggag actactgaga   5700
acagttttgg aaccaattag agatgcactt aatgcagtga cccagaatat aagaccggtt   5760
cagagtgtag cttcaagtag gagacacaag agatttgcgg gagtagtcct ggcaggtgcg   5820
gccctaggcg ttgccacagc tgctcagata acagccggca ttgcacttca ccagtccatg   5880
ctgaactctc aagccatcga caatctgaga gcgagcctgg aaactactaa tcaggcaatt   5940
```

gaggcaatca gacaagcagg gcaggagatg atattggctg ttcagggtgt ccaagactac 6000
atcaataatg agctgatacc gtctatgaac caactatctt gtgatttaat cggccagaag 6060
ctcgggctca aattgctcag atactataca gaaatcctgt cattatttgg ccccagctta 6120
cgggacccca tatctgcgga gatatctatc caggctttga gctatgcgct tggaggagac 6180
atcaataagg tgttagaaaa gctcggatac agtggaggtg atttactggg catcttagag 6240
agcagaggaa taaaggcccg gataactcac gtcgacacag agtcctactt cattgtcctc 6300
agtatagcct atccgacgct gtccgagatt aagggggtga ttgtccaccg gctagagggg 6360
gtctcgtaca acataggctc tcaagagtgg tataccactg tgcccaagta tgttgcaacc 6420
caagggtacc ttatctcgaa ttttgatgag tcatcgtgta ctttcatgcc agaggggact 6480
gtgtgcagcc aaaatgcctt gtacccgatg agtcctctgc tccaagaatg cctccggggg 6540
tccaccaagt cctgtgctcg tacactcgta tccgggtctt ttgggaaccg gttcatttta 6600
tcacaaggga acctaatagc caattgtgca tcaatccttt gcaagtgtta cacaacagga 6660
acgatcatta atcaagaccc tgacaagatc ctaacataca ttgctgccga tcactgcccg 6720
gtagtcgagg tgaacggcgt gaccatccaa gtcgggagca ggaggtatcc agacgctgtg 6780
tacttgcaca gaattgacct cggtcctccc atatcattgg agaggttgga cgtagggaca 6840
aatctgggga atgcaattgc taagttggag gatgccaagg aattgttgga gtcatcggac 6900
cagatattga ggagtatgaa aggtttatcg agcactagca tagtctacat cctgattgca 6960
gtgtgtcttg gagggttgat agggatcccc gctttaatat gttgctgcag ggggcgttgt 7020
aacaaaaagg gagaacaagt tggtatgtca agaccaggcc taaagcctga tcttacggga 7080
acatcaaaat cctatgtaag gtcgctctga tcctctacaa ctcttgaaac acaaatgtcc 7140
cacaagtctc ctcttcgtca tcaagcaacc accgcaccca gcatcaagcc cacctgaaat 7200
tatctccggt ttccctctgg ccgaacaata tcggtagtta attaaaactt agggtgcaag 7260
atcatccaca atgtcaccac aacgagaccg gataaatgcc ttctacaaag ataaccccca 7320
tcccaaggga agtaggatag tcattaacag agaacatctt atgattgata gaccttatgt 7380
tttgctggct gttctgtttg tcatgtttct gagcttgatc gggttgctag ccattgcagg 7440
cattagactt catcgggcag ccatctacac cgcagagatc cataaaagcc tcagcaccaa 7500
tctagatgta actaactcaa tcgagcatca ggtcaaggac gtgctgacac cactcttcaa 7560
aatcatcggt gatgaagtgg gcctgaggac acctcagaga ttcactgacc tagtgaaatt 7620
catctctgac aagattaaat tccttaatcc ggatagggag tacgacttca gagatctcac 7680
ttggtgtatc aacccgccag agagaatcaa attggattat gatcaatact gtgcagatgt 7740
ggctgctgaa gagctcatga atgcattggt gaactcaact ctactggaga ccagaacaac 7800
caatcagttc ctagctgtct caaagggaaa ctgctcaggg cccactacaa tcagaggtca 7860
attctcaaac atgtcgctgt ccctgttaga cttgtattta ggtcgaggtt acaatgtgtc 7920
atctatagtc actatgacat cccagggaat gtatggggga acttacctag tggaaaagcc 7980
taatctgagc agcaaaaggt cagagttgtc acaactgagc atgtaccgag tgtttgaagt 8040
aggtgttatc agaaatccgg gtttgggggc tccggtgttc catatgacaa actatcttga 8100
gcaaccagtc agtaatgatc tcagcaactg tatggtggct ttgggggagc tcaaactcgc 8160
agccctttgt cacggggaag attctatcac aattccctat cagggatcag ggaaaggtgt 8220
cagcttccag ctcgtcaagc taggtgtctg gaaatcccca accgacatgc aatcctgggt 8280
ccccttatca acggatgatc cagtgataga caggctttac ctctcatctc acagaggtgt 8340

-continued

```
tatcgctgac aaccaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
ggttagtccc tacctcttca ctgtcccaat taaggaagca ggcggagact gccatgcccc   8760
aacataccta cctgcggagg tggatggtga tgtcaaactc agttccaatc tggtgattct   8820
acctggtcaa gatctccaat atgttttggc aacctacgat acttccaggg ttgaacatgc   8880
tgtggtttat tacgtttaca gcccaagccg ctcattttct tacttttatc cttttaggtt   8940
gcctataaag gggtccccca tcgaattaca agtggaatgc ttcacatggg accaaaaact   9000
ctggtgccgt cacttctgtg tgcttgcgga ctcagaatct ggtggacata tcactcactc   9060
tgggatggtg ggcatgggag tcagctgcac agtcacccgg gaagatggaa ccaatcgcag   9120
atagggctgc tagtgaacca atcacatgat gtcacccaga catcaggcat acccactagt   9180
gtgaaataga catcagaatt aagaaaaacg tagggtccaa gtggttcccc gttatggact   9240
cgctatctgt caaccagatc ttataccctg aagttcacct agatagcccg atagttacca   9300
ataagatagt agccatcctg gagtatgctc gagtccctca cgcttacagc ctggaggacc   9360
ctacactgtg tcagaacatc aagcaccgcc taaaaaacgg attttccaac caaatgatta   9420
taaacaatgt ggaagttggg aatgtcatca agtccaagct taggagttat ccggcccact   9480
ctcatattcc atatccaaat tgtaatcagg atttatttaa catagaagac aaagagtcaa   9540
cgaggaagat ccgtgaactc ctcaaaaagg ggaattcgct gtactccaaa gtcagtgata   9600
aggttttcca atgcttaagg gacactaact cacggcttgg cctaggctcc gaattgaggg   9660
aggacatcaa ggagaaagtt attaacttgg gagtttacat gcacagctcc cagtggtttg   9720
agccctttct gttttggttt acagtcaaga ctgagatgag gtcagtgatt aaatcacaaa   9780
cccatacttg ccataggagg agacacacac ctgtattctt cactggtagt tcagttgagt   9840
tgctaatctc tcgtgacctt gttgctataa tcagtaaaga gtctcaacat gtatattacc   9900
tgacatttga actggttttg atgtattgtg atgtcataga ggggaggtta atgacagaga   9960
ccgctatgac tattgatgct aggtatacag agcttctagg aagagtcaga tacatgtgga  10020
aactgataga tggtttcttc cctgcactcg ggaatccaac ttatcaaatt gtagccatgc  10080
tggagcctct ttcacttgct tacctgcagc tgagggatat aacagtagaa ctcagaggtg  10140
ctttccttaa ccactgcttt actgaaatac atgatgttct tgaccaaaac gggttttctg  10200
atgaaggtac ttatcatgag ttaattgaag ctctagatta cattttcata actgatgaca  10260
tacatctgac aggggagatt ttctcatttt tcagaagttt cggccacccc agacttgaag  10320
cagtaacggc tgctgaaaat gttaggaaat acatgaatca gcctaaagtc attgtgtatg  10380
agactctgat gaaaggtcat gccatatttt gtggaatcat aatcaacggc tatcgtgaca  10440
ggcacggagg cagttggcca ccgctgaccc tcccccctgca tgctgcagac acaatccgga  10500
atgctcaagc ttcaggtgat gggttaacac atgagcagtg cgttgataac tggaaatctt  10560
ttgctggagt gaaatttggc tgctttatgc ctcttagcct ggatagtgat ctgacaatgt  10620
acctaaagga caaggcactt gctgctctcc aaagggaatg ggattcagtt tacccgaaag  10680
```

agttcctgcg ttacgaccct cccaagggaa ccgggtcacg gaggcttgta gatgttttcc 10740
ttaatgattc gagctttgac ccatatgatg tgataatgta tgttgtaagt ggagcttacc 10800
tccatgaccc tgagttcaac ctgtcttaca gcctgaaaga aaaggagatc aaggaaacag 10860
gtagactttt tgctaaaatg acttacaaaa tgagggcatg ccaagtgatt gctgaaaatc 10920
taatctcaaa cgggattggc aaatatttta aggacaatgg gatggccaag gatgagcacg 10980
atttgactaa ggcactccac actctagctg tctcaggagt ccccaaagat ctcaaagaaa 11040
gtcacagggg ggggccagtc ttaaaaacct actcccgaag cccagtccac acaagtacca 11100
ggaacgtgag agcagcaaaa gggtttatag ggttccctca agtaattcgg caggaccaag 11160
acactgatca tccggagaat atggaagctt acgagacagt cagtgcattt atcacgactg 11220
atctcaagaa gtactgcctt aattggagat atgagaccat cagcttgttt gcacagaggc 11280
taaatgagat ttacggattg ccctcatttt tccagtggct gcataagagg cttgagacct 11340
ctgtcctgta tgtaagtgac cctcattgcc cccccgacct tgacgcccat atcccgttat 11400
ataaagtccc caatgatcaa atcttcatta agtaccctat gggaggtata gaagggtatt 11460
gtcagaagct gtggaccatc agcaccattc cctatctata cctggctgct tatgagagcg 11520
gagtaaggat tgcttcgtta gtgcaagggg acaatcagac catagccgta acaaaaaggg 11580
tacccagcac atggccctac aaccttaaga aacgggaagc tgctagagta actagagatt 11640
actttgtaat tcttaggcaa aggctacatg atattggcca tcacctcaag gcaaatgaga 11700
caattgtttc atcacatttt tttgtctatt caaaaggaat atattatgat gggctacttg 11760
tgtcccaatc actcaagagc atcgcaagat gtgtattctg gtcagagact atagttgatg 11820
aaacaagggc agcatgcagt aatattgcta caacaatggc taaaagcatc gagagaggtt 11880
atgaccgtta ccttgcatat tccctgaacg tcctaaaagt gatacagcaa attctgatct 11940
ctcttggctt cacaatcaat tcaaccatga cccgggatgt agtcataccc ctcctcacaa 12000
acaacgacct cttaataagg atggcactgt tgcccgctcc tattgggggg atgaattatc 12060
tgaatatgag caggctgttt gtcagaaaca tcggtgatcc agtaacatca tcaattgctg 12120
atctcaagag aatgattctc gcctcactaa tgcctgaaga gaccctccat caggtaatga 12180
cacaacaacc gggggactct tcattcctag actgggctag cgacccttac tcagcaaatc 12240
ttgtatgtgt ccagagcatc actagactcc tcaagaacat aactgcaagg tttgtcctga 12300
tccatagtcc aaacccaatg ttaaaaggat tattccatga tgacagtaaa gaagaggacg 12360
agggactggc ggcattcctc atggacaggc atattatagt acctagggca gctcatgaaa 12420
tcctggatca tagtgtcaca ggggcaagag agtctattgc aggcatgctg gataccacaa 12480
aaggcttgat tcgagccagc atgaggaagg ggggtttaac ctctcgagtg ataaccagat 12540
tgtccaatta tgactatgaa caattcagag cagggatggt gctattgaca ggaagaaaga 12600
gaaatgtcct cattgacaaa gagtcatgtt cagtgcagct ggcgagagct ctaagaagcc 12660
atatgtgggc gaggctagct cgaggacggc ctatttacgg ccttgaggtc cctgatgtac 12720
tagaatctat gcgaggccac cttattcggc gtcatgagac atgtgtcatc tgcgagtgtg 12780
gatcagtcaa ctacggatgg ttttttgtcc cctcgggttg ccaactggat gatattgaca 12840
aggaaacatc atccttgaga gtcccatata ttggttctac cactgatgag agaacagaca 12900
tgaagcttgc cttcgtaaga gccccaagtc gatccttgcg atctgctgtt agaatagcaa 12960
cagtgtactc atgggcttac ggtgatgatg atagctcttg gaacgaagcc tggttgttgg 13020
ctaggcaaag ggccaatgtg agcctggagg agctaagggt gatcactccc atctcaactt 13080

-continued

```
cgactaattt agcgcatagg ttgagggatc gtagcactca agtgaaatac tcaggtacat  13140
cccttgtccg agtggcgagg tataccacaa tctccaacga caatctctca tttgtcatat  13200
cagataagaa ggttgatact aactttatat accaacaagg aatgcttcta gggttgggtg  13260
ttttagaaac attgtttcga ctcgagaaag ataccggatc atctaacacg gtattacatc  13320
ttcacgtcga aacagattgt tgcgtgatcc cgatgataga tcatcccagg atacccagct  13380
cccgcaagct agagctgagg gcagagctat gtaccaaccc attgatatat gataatgcac  13440
ctttaattga cagagatgca acaaggctat acacccagag ccataggagg caccttgtgg  13500
aatttgttac atggtccaca ccccaactat atcacatttt agctaagtcc acagcactat  13560
ctatgattga cctggtaaca aaatttgaga aggaccatat gaatgaaatt tcagctctca  13620
taggggatga cgatatcaat agtttcataa ctgagtttct gctcatagag ccaagattat  13680
tcactatcta cttgggccag tgtgcggcca tcaattgggc atttgatgta cattatcata  13740
gaccatcagg gaaatatcag atgggtgagc tgttgtcatc gttcctttct agaatgagca  13800
aaggagtgtt taaggtgctt gtcaatgctc taagccaccc aaagatctac aagaaattct  13860
ggcattgtgg tattatagag cctatccatg gtccttcact tgatgctcaa aacttgcaca  13920
caactgtgtg caacatggtt tacacatgct atatgaccta cctcgacctg ttgttgaatg  13980
aagagttaga agagttcaca tttctcttgt gtgaaagcga cgaggatgta gtaccggaca  14040
gattcgacaa catccaggca aaacacttat gtgttctggc agatttgtac tgtcaaccag  14100
ggacctgccc accaattcaa ggtctaagac cggtagagaa atgtgcagtt ctaaccgacc  14160
atatcaaggc agaggctatg ttatctccag caggatcttc gtggaacata aatccaatta  14220
ttgtagacca ttactcatgc tccctgactt atctccggcg aggatcgatc aaacagataa  14280
gattgagagt tgatccagga ttcattttcg acgccctcgc tgaggtaaat gtcagtcagc  14340
caaagatcgg cagcaacaac atctcaaata tgagcatcaa ggctttcaga cccccacacg  14400
atgatgttgc aaaattgctc aaagatatca acacaagcaa gcacaatctt cccatttcag  14460
ggggcaatct cgccaattat gaaatccatg ctttccgcag aatcgggttg aactcatctg  14520
cttgctacaa agctgttgag atatcaacat taattaggag atgccttgag ccaggggagg  14580
acggcttgtt cttgggtgag ggatcgggtt ctatgttgat cacttataag gagatactta  14640
aactaagcaa gtgcttctat aatagtgggg tttccgccaa ttctagatct ggtcaaaggg  14700
aattagcacc ctatccctcc gaagttggcc ttgtcgaaca cagaatggga gtaggtaata  14760
ttgtcaaagt gctctttaac gggaggcccg aagtcacgtg ggtaggcagt gtagattgct  14820
tcaatttcat agttagtaat atccctacct ctagtgtggg gtttatccat tcagatatag  14880
agaccttgcc tgacaaagat actatagaga agctagagga attggcagcc atcttatcga  14940
tggctctgct cctgggcaaa ataggatcaa tactggtgat taagcttatg cctttcagcg  15000
gggattttgt tcagggattt ataagttatg tagggtctca ttatagagaa gtgaaccttg  15060
tataccctag atacagcaac ttcatatcta ctgaatctta tttggttatg acagatctca  15120
aggctaaccg gctaatgaat cctgaaaaga ttaagcagca gataattgaa tcatctgtga  15180
ggacttcacc tggacttata ggtcacatcc tatccattaa gcaactaagc tgcatacaag  15240
caattgtggg agacgcagtt agtagaggtg atatcaatcc tactctgaaa aaacttacac  15300
ctatagagca ggtgctgatc aattgcgggt tggcaattaa cggacctaag ctgtgcaaag  15360
aattgatcca ccatgatgtt gcctcagggc aagatggatt gcttaattct atactcatcc  15420
```

```
tctacaggga gttggcaaga ttcaaagaca accaaagaag tcaacaaggg atgttccacg  15480

cttaccccgt attggtaagt agcaggcaac gagaacttat atctaggatc acccgcaaat  15540

tttgggggca cattcttctt tactccggga acagaaagtt gataaataag tttatccaga  15600

atctcaagtc cggctatctg atactagact tacaccagaa tatcttcgtt aagaatctat  15660

ccaagtcaga gaaacagatt attatgacgg ggggtttgaa acgtgagtgg gtttttaagg  15720

taacagtcaa ggagaccaaa gaatggtata agttagtcgg atacagtgcc ctgattaagg  15780

actaattggt tgaactccgg aaccctaatc ctgccctagg tggttaggca ttatttgcaa  15840

tatattaaag aaaactttga aaatacgaag tttctattcc cagctttgtc tggt        15894


<210> SEQ ID NO 2
<211> LENGTH: 15894
<212> TYPE: DNA
<213> ORGANISM: Measles virus attenuated strain
<220> FEATURE:
<223> OTHER INFORMATION: Description: cDNA of Measles virus attenuated
      strain

<400> SEQUENCE: 2

accaaacaaa gttgggtaag gatagttcaa tcaatgatca tcttctagtg cacttaggat     60

tcaagatcct attatcaggg acaagagcag gattagggat atccgagatg gccacacttt    120

taaggagctt agcattgttc aaaagaaaca aggacaaacc acccattaca tcaggatccg    180

gtggagccat cagaggaatc aaacacatta ttatagtacc aatccctgga gattcctcaa    240

ttaccactcg atccagactt ctggaccggt tggtcaggtt aattggaaac ccggatgtga    300

gcgggcccaa actaacaggg gcactaatag gtatattatc cttatttgtg gagtctccag    360

gtcaattgat tcagaggatc accgatgacc ctgacgttag cataaggctg ttagaggttg    420

tccagagtga ccagtcacaa tctggcctta ccttcgcatc aagaggtacc aacatggagg    480

atgaggcgga ccaatacttt tcacatgatg atccaattag tagtgatcaa tccaggttcg    540

gatggttcga gaacaaggaa atctcagata ttgaagtgca agaccctgag ggattcaaca    600

tgattctggg taccatccta gcccaaattt gggtcttgct cgcaaaggcg gttacggccc    660

cagacacggc agctgattcg gagctaagaa ggtggataaa gtacacccaa caaagaaggg    720

tagttggtga atttagattg gagagaaaat ggttggatgt ggtgaggaac aggattgccg    780

aggacctctc cttacgccga ttcatggtcg ctctaatcct ggatatcaag agaacacccg    840

gaaacaaacc caggattgct gaaatgatat gtgacattga tacatatatc gtagaggcag    900

gattagccag ttttatcctg actattaagt ttgggataga aactatgtat cctgctcttg    960

gactgcatga atttgctggt gagttatcca cacttgagtc cttgatgaac ctttaccagc   1020

aaatggggga aactgcaccc tacatggtaa tcctggagaa ctcaattcag aacaagttca   1080

gtgcaggatc ataccctctg ctctggagct atgccatggg agtaggagtg gaacttgaaa   1140

actccatggg aggtttgaac tttggccgat cttactttga tccagcatat tttagattag   1200

ggcaagagat ggtaaggagg tcagctggaa aggtcagttc cacattggca tctgaactcg   1260

gtatcactgc cgaggatgca aggcttgttt cagagattgc aatgcatact actgaggaca   1320

agatcagtag agcggttgga cccagacaag cccaagtatc atttctacac ggtgatcaaa   1380

gtgagaatga gctaccgaga ttgggggggca aggaagatag gagggtcaaa cagagtcgag   1440

gagaagccag ggagagctac agagaaaccg ggcccagcag agcaagtgat gcgagagctg   1500

cccatcttcc aaccggcaca cccctagaca ttgacactgc atcggagtcc agccaagatc   1560
```

cgcaggacag tcgaaggtca gctgacgccc tgcttaggct gcaagccatg gcaggaatct 1620
cggaagaaca aggctcagac acggacaccc ctatagtgta caatgacaga aatcttctag 1680
actaggtgcg agatgccgag gaccagaaca acatccgcct accctccatc attgttataa 1740
aaaacttagg aaccaggtcc acacagccgc cagcccatca accatccact cccacgattg 1800
gagcagatgg cagaagagca ggcacgccat gtcaaaaacg gactggaatg catccgggct 1860
ctcaaggccg agcccatcgg ctcactggcc atcgaggaag ctatggcagc atggtcagaa 1920
atatcagaca acccaggaca ggagcgagcc acctgcaggg aagagaaggc aggcagttcg 1980
ggtctcagca aaccatgcct ctcagcaatt ggatcaactg aaggcggtgc acctcgcatc 2040
cgcggtcagg gacctggaga gagcgatgac gacgctgaaa ctttgggaat ccccccaaga 2100
aatctccagg catcaagcac tgggctacag tgtcattatg tttatgatca cagcggtgaa 2160
gcggttaagg gaatccaaga tgctgactct atcatggttc aatcaggcct tgatggtgat 2220
agcaccctct caggaggaga caatgaatct gaaaacagcg atgtggatat tggcgaacct 2280
gataccgagg gatatgctat cactgaccgg ggatctgctc ccatctctat ggggttcagg 2340
gcttctgatg ttgaaactgc agaaggaggg gagatccacg agctcctgag actccaatcc 2400
agaggcaaca actttccgaa gcttgggaaa actctcaatg ttcctccgcc cccggacccc 2460
ggtagggcca gcacttccgg gacacccatt aaaaagggca cagacgcgag attagcctca 2520
tttggaacgg agatcgcgtc ttcattgaca ggtggtgcaa cccaatgtgc tcgaaagtca 2580
ccctcggaac catcagggcc aggtgcacct gcggggaacg tccccgagtg tgtgagcaat 2640
gccgcactga tacaggagtg gacacccgaa tctggcacca caatctcccc gagatcccag 2700
aataatgaag aagggggaga ccattatgat gatgagctgt tctctgatgt ccaagatatt 2760
aaaacagcct tggccaaaat acacgaggat aatcagaaga taatctccaa gctagaatca 2820
ctgctgttat tgaagggaga agttgagtca attaagaagc agatcaacag gcaaaatatc 2880
agcatatcca ccctggaagg acacctctca agcatcatga tcgccattcc tggacttggg 2940
aaggatccca acgaccccac tgcagatgtc gaaatcaatc ccgacttgaa acccatcata 3000
ggcagagatt caggccgagc actggccgaa gttctcaaga aacccgttgc cagccgacaa 3060
ctccaaggaa tgacaaatgg acggaccagt tccagaggac agctgctgaa ggaatttcag 3120
ctaaagccga tcgggaaaaa gatgagctca gccgtcgggt ttgttcctga caccggccct 3180
gcatcacgca gtgtaatccg ctccattata aaatccagcc ggctagagga ggatcggaag 3240
cgttacctga tgactctcct tgatgatatc aaaggagcca atgatcttgc caagttccac 3300
cagatgctgg tgaagataat aatgaagtag ctacagctca acttacctgc caaccccatg 3360
ccagtcgacc caactagtac aacctaaatc cattataaaa aacttaggag caaagtgatt 3420
gcctcccaag ttccacaatg acagagatct acgacttcga caagtcggca tgggacatca 3480
aagggtcgat cgctccgata caacccacca cctacagtga tggcaggctg gtgccccagg 3540
tcagagtcat agatcctggt ctaggcgaca ggaaggatga atgctttatg tacatgtttc 3600
tgctgggggt tgttgaggac agcgattccc tagggcctcc aatcgggcga gcatttgggt 3660
ccctgccctt aggtgttggc agatccacag caaagcccga aaaactcctc aaagaggcca 3720
ctgagcttga catagttgtt agacgtacag cagggctcaa tgaaaaactg gtgttctaca 3780
acaacacccc actaactctc ctcacacctt ggagaaaggt cctaacaaca gggagtgtct 3840
tcaacgcaaa ccaagtgtgc aatgcggtta atctgatacc gctcgatacc ccgcagaggt 3900
tccgtgttgt ttatatgagc atcacccgtc tttcggataa cgggtattac accgttcctg 3960
gaagaatgct ggaattcaga tcggtcaatg cagtggcctt caacctgctg gtgaccctta 4020
ggattgacaa ggcgataggc cctgggaaga tcatcgacaa tacagagcaa cttcctgagg 4080
caacatttat ggtccacatc gggaacttca ggagaaagaa gagtgaagtc tactctgccg 4140
attattgcaa aatgaaaatc gaaaagatgg gcctggtttt tgcacttggt gggatagggg 4200
gcaccagtct tcacattaga agcacaggca aaatgagcaa gactctccat gcacaactcg 4260
ggttcaagaa gaccttatgt tacccgctga tggatatcaa tgaagacctt aatcgattac 4320
tctggaggag cagatgcaag atagtaagaa tccaggcagt tttgcagcca tcagttcctc 4380
aagaattccg catttacgac gacgtgatca taaatgatga ccaaggacta ttcaaagttc 4440
tgtagaccgt agtgcccagc aatgcccgaa aacgaccccc ctcacaatga cagccagaag 4500
gcccggacaa aaaagccccc tccgaaagac tccacggacc aagcgagagg ccagccagca 4560
gccgacggca agcgcgaaca ccaggcggcc ccagcacaga acagccctga cacaaggcca 4620
ccaccagcca ccccaatctg catcctcctc gtgggacccc cgaggaccaa cccccaaggc 4680
tgcccccgat ccaaaccacc aaccgcatcc ccaccacccc cgggaaagaa acccccagca 4740
attggaaggc ccctccccct cttcctcaac acaagaactc cacaaccgaa ccgcacaagc 4800
gaccgaggtg acccaaccgc aggcatccga ctccctagac agatcctctc tccccggcaa 4860
actaaacaaa acttagggcc aaggaacata cacacccaac agaacccaga ccccggccca 4920
cggcgccgcg cccccaaccc ccgacaacca gagggagccc ccaaccaatc ccgccggctc 4980
ccccggtgcc cacaggcagg gacaccaacc cccgaacaga cccagcaccc aaccatcgac 5040
aatccaagac ggggggcccc ccccaaaaaa aggcccccag gggccgacag ccagcaccgc 5100
gaggaagccc acccacccca cacacgacca cggcaaccaa accagaaccc agaccaccct 5160
gggccaccag ctcccagact cggccatcac cccgcagaaa ggaaaggcca caacccgcgc 5220
accccagccc cgatccggcg gggagccacc caacccgaac cagcacccaa gagcgatccc 5280
cgaaggaccc ccgaaccgca aaggacatca gtatcccaca gcctctccaa gtcccccggt 5340
ctcctcctct tctcgaaggg accaaaagat caatccacca cacccgacga cactcaactc 5400
cccaccccta aaggagacac cgggaatccc agaatcaaga ctcatccaat gtccatcatg 5460
ggtctcaagg tgaacgtctc tgccatattc atggcagtac tgttaactct ccaaacaccc 5520
accggtcaaa tccattgggg caatctctct aagatagggg tggtaggaat aggaagtgca 5580
agctacaaag ttatgactcg ttccagccat caatcattag tcataaaatt aatgcccaat 5640
ataactctcc tcaataactg cacgagggta gagattgcag aatacaggag actactgaga 5700
acagttttgg aaccaattag agatgcactt aatgcagtga cccagaatat aagaccggtt 5760
cagagtgtag cttcaagtag gagacacaag agatttgcgg gagtagtcct ggcaggtgcg 5820
gccctaggcg ttgccacagc tgctcagata acagccggca ttgcacttca ccagtccatg 5880
ctgaactctc aagccatcga caatctgaga gcgagcctgg aaactactaa tcaggcaatt 5940
gaggcaatca gacaagcagg gcaggagatg atattggctg ttcagggtgt ccaagactac 6000
atcaataatg agctgatacc gtctatgaac caactatctt gtgatttaat cggccagaag 6060
ctcgggctca aattgctcag atactataca gaaatcctgt cattatttgg ccccagctta 6120
cgggacccca tatctgcgga gatatctatc caggctttga gctatgcgct tggaggagac 6180
atcaataagg tgttagaaaa gctcggatac agtggaggtg atttactggg catcttagag 6240
agcagaggaa taaaggcccg gataactcac gtcgacacag agtcctactt cattgtcctc 6300

```
agtatagcct atccgacgct gtccgagatt aagggggtga ttgtccaccg gctagagggg   6360
gtctcgtaca acataggctc tcaagagtgg tataccactg tgcccaagta tgttgcaacc   6420
caagggtacc ttatctcgaa ttttgatgag tcatcgtgta ctttcatgcc agaggggact   6480
gtgtgcagcc aaaatgcctt gtacccgatg agtcctctgc tccaagaatg cctccggggg   6540
tccaccaagt cctgtgctcg tacactcgta tccgggtctt ttgggaaccg gttcatttta   6600
tcacaaggga acctaatagc caattgtgca tcaatccttt gcaagtgtta cacaacagga   6660
acgatcatta atcaagaccc tgacaagatc ctaacataca ttgctgccga tcactgcccg   6720
gtagtcgagg tgaacggcgt gaccatccaa gtcgggagca ggaggtatcc agacgctgtg   6780
tacttgcaca gaattgacct cggtcctccc atatcattgg agaggttgga cgtagggaca   6840
aatctgggga atgcaattgc taagttggag gatgccaagg aattgttgga gtcatcggac   6900
cagatattga ggagtatgaa aggtttatcg agcactagca tagtctacat cctgattgca   6960
gtgtgtcttg gagggttgat agggatcccc gctttaatat gttgctgcag gggcgttgt   7020
aacaaaaagg gagaacaagt tggtatgtca agaccaggcc taaagcctga tcttacggga   7080
acatcaaaat cctatgtaag gtcgctctga tcctctacaa ctcttgaaac acaaatgtcc   7140
cacaagtctc ctcttcgtca tcaagcaacc accgcaccca gcatcaagcc cacctgaaat   7200
tatctccggt ttccctctgg ccgaacaata tcggtagtta attaaaactt agggtgcaag   7260
atcatccaca atgtcaccac aacgagaccg gataaatgcc ttctacaaag ataaccccca   7320
tcccaaggga agtaggatag tcattaacag agaacatctt atgattgata gaccttatgt   7380
tttgctggct gttctgtttg tcatgtttct gagcttgatc gggttgctag ccattgcagg   7440
cattagactt catcgggcag ccatctacac cgcagagatc cataaaagcc tcagcaccaa   7500
tctagatgta actaactcaa tcgagcatca ggtcaaggac gtgctgacac cactcttcaa   7560
aatcatcggt gatgaagtgg gcctgaggac acctcagaga ttcactgacc tagtgaaatt   7620
catctctgac aagattaaat tccttaatcc ggatagggag tacgacttca gagatctcac   7680
ttggtgtatc aacccgccag agagaatcaa attggattat gatcaatact gtgcagatgt   7740
ggctgctgaa gagctcatga atgcattggt gaactcaact ctactggaga ccagaacaac   7800
caatcagttc ctagctgtct caaagggaaa ctgctcaggg cccactacaa tcagaggtca   7860
attctcaaac atgtcgctgt ccctgttaga cttgtattta ggtcgaggtt acaatgtgtc   7920
atctatagtc actatgacat cccagggaat gtatgggga acttacctag tggaaaagcc   7980
taatctgagc agcaaaaggt cagagttgtc acaactgagc atgtaccgag tgtttgaagt   8040
aggtgttatc agaaatccgg gtttgggggc tccggtgttc catatgacaa actatcttga   8100
gcaaccagtc agtaatgatc tcagcaactg tatggtggct ttgggggagc tcaaactcgc   8160
agccctttgt cacggggaag attctatcac aattccctat cagggatcag ggaaaggtgt   8220
cagcttccag ctcgtcaagc taggtgtctg gaaatcccca accgacatgc aatcctgggt   8280
ccccttatca acggatgatc cagtgataga caggctttac ctctcatctc acagaggtgt   8340
tatcgctgac aaccaagcaa aatgggctgt cccgacaaca cgaacagatg acaagttgcg   8400
aatggagaca tgcttccaac aggcgtgtaa gggtaaaatc caagcactct gcgagaatcc   8460
cgagtgggca ccattgaagg ataacaggat tccttcatac ggggtcttgt ctgttgatct   8520
gagtctgaca gttgagctta aaatcaaaat tgcttcggga ttcgggccat tgatcacaca   8580
cggttcaggg atggacctat acaaatccaa ccacaacaat gtgtattggc tgactatccc   8640
gccaatgaag aacctagcct taggtgtaat caacacattg gagtggatac cgagattcaa   8700
```

ggttagtccc tacctcttca ctgtcccaat taaggaagca ggcggagact gccatgcccc 8760
aacataccta cctgcggagg tggatggtga tgtcaaactc agttccaatc tggtgattct 8820
acctggtcaa gatctccaat atgttttggc aacctacgat acttccaggg ttgaacatgc 8880
tgtggtttat tacgtttaca gcccaagccg ctcattttct tacttttatc cttttaggtt 8940
gcctataaag gggtccccca tcgaattaca agtggaatgc ttcacatggg accaaaaact 9000
ctggtgccgt cacttctgtg tgcttgcgga ctcagaatct ggtggacata tcactcactc 9060
tgggatggtg ggcatgggag tcagctgcac agtcacccgg gaagatggaa ccaatcgcag 9120
atagggctgc tagtgaacca atcacatgat gtcacccaga catcaggcat acccactagt 9180
gtgaaataga catcagaatt aagaaaaacg tagggtccaa gtggttcccc gttatggact 9240
cgctatctgt caaccagatc ttataccctg aagttcacct agatagcccg atagttacca 9300
ataagatagt agccatcctg gagtatgctc gagtccctca cgcttacagc ctggaggacc 9360
ctacactgtg tcagaacatc aagcaccgcc taaaaaacgg attttccaac caaatgatta 9420
taaacaatgt ggaagttggg aatgtcatca agtccaagct taggagttat ccggcccact 9480
ctcatattcc atatccaaat tgtaatcagg atttatttaa catagaagac aaagagtcaa 9540
cgaggaagat ccgtgaactc ctcaaaaagg ggaattcgct gtactccaaa gtcagtgata 9600
aggttttcca atgcttaagg gacactaact cacggcttgg cctaggctcc gaattgaggg 9660
aggacatcaa ggagaaagtt attaacttgg gagtttacat gcacagctcc cagtggtttg 9720
agccctttct gttttggttt acagtcaaga ctgagatgag gtcagtgatt aaatcacaaa 9780
cccatacttg ccataggagg agacacacac ctgtattctt cactggtagt tcagttgagt 9840
tgctaatctc tcgtgacctt gttgctataa tcagtaaaga gtctcaacat gtatattacc 9900
tgacatttga actggttttg atgtattgtg atgtcataga ggggaggtta atgacagaga 9960
ccgctatgac tattgatgct aggtatacag agcttctagg aagagtcaga tacatgtgga 10020
aactgataga tggtttcttc cctgcactcg ggaatccaac ttatcaaatt gtagccatgc 10080
tggagcctct ttcacttgct tacctgcagc tgagggatat aacagtagaa ctcagaggtg 10140
ctttccttaa ccactgcttt actgaaatac atgatgttct tgaccaaaac gggttttctg 10200
atgaaggtac ttatcatgag ttaattgaag ctctagatta cattttcata actgatgaca 10260
tacatctgac aggggagatt ttctcatttt tcagaagttt cggccacccc agacttgaag 10320
cagtaacggc tgctgaaaat gttaggaaat acatgaatca gcctaaagtc attgtgtatg 10380
agactctgat gaaaggtcat gccatatttt gtggaatcat aatcaacggc tatcgtgaca 10440
ggcacggagg cagttggcca ccgctgaccc tcccccctgca tgctgcagac acaatccgga 10500
atgctcaagc ttcaggtgat gggttaacac atgagcagtg cgttgataac tggaaatctt 10560
ttgctggagt gaaatttggc tgctttatgc ctcttagcct ggatagtgat ctgacaatgt 10620
acctaaagga caaggcactt gctgctctcc aaagggaatg ggattcagtt tacccgaaag 10680
agttcctgcg ttacgaccct cccaagggaa ccgggtcacg gaggcttgta gatgttttcc 10740
ttaatgattc gagctttgac ccatatgatg tgataatgta tgttgtaagt ggagcttacc 10800
tccatgaccc tgagttcaac ctgtcttaca gcctgaaaga aaaggagatc aaggaaacag 10860
gtagactttt tgctaaaatg acttacaaaa tgagggcatg ccaagtgatt gctgaaaatc 10920
taatctcaaa cgggattggc aaatatttta aggacaatgg gatggccaag gatgagcacg 10980
atttgactaa ggcactccac actctagctg tctcaggagt ccccaaagat ctcaaagaaa 11040

```
gtcacagggg ggggccagtc ttaaaaacct actcccgaag cccagtccac acaagtacca  11100
ggaacgtgag agcagcaaaa gggtttatag ggttccctca agtaattcgg caggaccaag  11160
acactgatca tccggagaat atggaagctt acgagacagt cagtgcattt atcacgactg  11220
atctcaagaa gtactgcctt aattggagat atgagaccat cagcttgttt gcacagaggc  11280
taaatgagat ttacggattg ccctcatttt tccagtggct gcataagagg cttgagacct  11340
ctgtcctgta tgtaagtgac cctcattgcc cccccgacct tgacgcccat atcccgttat  11400
ataaagtccc caatgatcaa atcttcatta agtaccctat gggaggtata gaagggtatt  11460
gtcagaagct gtggaccatc agcaccattc cctatctata cctggctgct tatgagagcg  11520
gagtaaggat tgcttcgtta gtgcaagggg acaatcagac catagccgta acaaaaaggg  11580
tacccagcac atggccctac aaccttaaga aacgggaagc tgctagagta actagagatt  11640
actttgtaat tcttaggcaa aggctacatg atattggcca tcacctcaag gcaaatgaga  11700
caattgtttc atcacatttt tttgtctatt caaaaggaat atattatgat gggctacttg  11760
tgtcccaatc actcaagagc atcgcaagat gtgtattctg gtcagagact atagttgatg  11820
aaacaagggc agcatgcagt aatattgcta caacaatggc taaaagcatc gagagaggtt  11880
atgaccgtta ccttgcatat tccctgaacg tcctaaaagt gatacagcaa attctgatct  11940
ctcttggctt cacaatcaat tcaaccatga cccgggatgt agtcataccc ctcctcacaa  12000
acaacgacct cttaataagg atggcactgt tgcccgctcc tattgggggg atgaattatc  12060
tgaatatgag caggctgttt gtcagaaaca tcggtgatcc agtaacatca tcaattgctg  12120
atctcaagag aatgattctc gcctcactaa tgcctgaaga gaccctccat caggtaatga  12180
cacaacaacc gggggactct tcattcctag actgggctag cgacccttac tcagcaaatc  12240
ttgtatgtgt ccagagcatc actagactcc tcaagaacat aactgcaagg tttgtcctga  12300
tccatagtcc aaacccaatg ttaaaaggat tattccatga tgacagtaaa gaagaggacg  12360
agggactggc ggcattcctc atggacaggc atattatagt acctagggca gctcatgaaa  12420
tcctggatca tagtgtcaca ggggcaagag agtctattgc aggcatgctg gataccacaa  12480
aaggcttgat tcgagccagc atgaggaagg ggggtttaac ctctcgagtg ataaccagat  12540
tgtccaatta tgactatgaa caattcagag cagggatggt gctattgaca ggaagaaaga  12600
gaaatgtcct cattgacaaa gagtcatgtt cagtgcagct ggcgagagct ctaagaagcc  12660
atatgtgggc gaggctagct cgaggacggc ctatttacgg ccttgaggtc cctgatgtac  12720
tagaatctat gcgaggccac cttattcggc gtcatgagac atgtgtcatc tgcgagtgtg  12780
gatcagtcaa ctacggatgg ttttttgtcc cctcgggttg ccaactggat gatattgaca  12840
aggaaacatc atccttgaga gtcccatata ttggttctac cactgatgag agaacagaca  12900
tgaagcttgc cttcgtaaga gccccaagtc gatccttgcg atctgctgtt agaatagcaa  12960
cagtgtactc atgggcttac ggtgatgatg atagctcttg gaacgaagcc tggttgttgg  13020
ctaggcaaag ggccaatgtg agcctggagg agctaagggt gatcactccc atctcaactt  13080
cgactaattt agcgcatagg ttgagggatc gtagcactca agtgaaatac tcaggtacat  13140
cccttgtccg agtggcgagg tataccacaa tctccaacga caatctctca tttgtcatat  13200
cagataagaa ggttgatact aactttatat accaacaagg aatgcttcta gggttgggtg  13260
ttttagaaac attgtttcga ctcgagaaag ataccggatc atctaacacg gtattacatc  13320
ttcacgtcga aacagattgt tgcgtgatcc cgatgataga tcatcccagg atacccagct  13380
cccgcaagct agagctgagg gcagagctat gtaccaaccc attgatatat gataatgcac  13440
```

-continued ctttaattga cagagatgca acaaggctat acacccagag ccataggagg caccttgtgg 13500
aatttgttac atggtccaca ccccaactat atcacatttt agctaagtcc acagcactat 13560
ctatgattga cctggtaaca aaatttgaga aggaccatat gaatgaaatt tcagctctca 13620
taggggatga cgatatcaat agtttcataa ctgagtttct gctcatagag ccaagattat 13680
tcactatcta cttgggccag tgtgcggcca tcaattgggc atttgatgta cattatcata 13740
gaccatcagg gaaatatcag atgggtgagc tgttgtcatc gttcctttct agaatgagca 13800
aaggagtgtt taaggtgctt gtcaatgctc taagccaccc aaagatctac aagaaattct 13860
ggcattgtgg tattatagag cctatccatg gtccttcact tgatgctcaa aacttgcaca 13920
caactgtgtg caacatggtt tacacatgct atatgaccta cctcgacctg ttgttgaatg 13980
aagagttaga agagttcaca tttctcttgt gtgaaagcga cgaggatgta gtaccggaca 14040
gattcgacaa catccaggca aaacacttat gtgttctggc agatttgtac tgtcaaccag 14100
ggacctgccc accaattcaa ggtctaagac cggtagagaa atgtgcagtt ctaaccgacc 14160
atatcaaggc agaggctatg ttatctccag caggatcttc gtggaacata aatccaatta 14220
ttgtagacca ttactcatgc tccctgactt atctccggcg aggatcgatc aaacagataa 14280
gattgagagt tgatccagga ttcattttcg acgccctcgc tgaggtaaat gtcagtcagc 14340
caaagatcgg cagcaacaac atctcaaata tgagcatcaa ggctttcaga cccccacacg 14400
atgatgttgc aaaattgctc aaagatatca acacaagcaa gcacaatctt cccatttcag 14460
ggggcaatct cgccaattat gaaatccatg ctttccgcag aatcgggttg aactcatctg 14520
cttgctacaa agctgttgag atatcaacat taattaggag atgccttgag ccaggggagg 14580
acggcttgtt cttgggtgag ggatcgggtt ctatgttgat cacttataag gagatactta 14640
aactaagcaa gtgcttctat aatagtgggg tttccgccaa ttctagatct ggtcaaaggg 14700
aattagcacc ctatccctcc gaagttggcc ttgtcgaaca cagaatggga gtaggtaata 14760
ttgtcaaagt gctctttaac gggaggcccg aagtcacgtg ggtaggcagt gtagattgct 14820
tcaatttcat agttagtaat atccctacct ctagtgtggg gtttatccat tcagatatag 14880
agaccttgcc tgacaaagat actatagaga agctagagga attggcagcc atcttatcga 14940
tggctctgct cctgggcaaa ataggatcaa tactggtgat taagcttatg cctttcagcg 15000
gggattttgt tcagggattt ataagttatg tagggtctca ttatagagaa gtgaaccttg 15060
tataccctag atacagcaac ttcatatcta ctgaatctta tttggttatg acagatctca 15120
aggctaaccg gctaatgaat cctgaaaaga ttaagcagca gataattgaa tcatctgtga 15180
ggacttcacc tggacttata ggtcacatcc tatccattaa gcaactaagc tgcatacaag 15240
caattgtggg agacgcagtt agtagaggtg atatcaatcc tactctgaaa aaacttacac 15300
ctatagagca ggtgctgatc aattgcgggt tggcaattaa cggacctaag ctgtgcaaag 15360
aattgatcca ccatgatgtt gcctcagggc aagatggatt gcttaattct atactcatcc 15420
tctacaggga gttggcaaga ttcaaagaca accaaagaag tcaacaaggg atgttccacg 15480
cttaccccgt attggtaagt agcaggcaac gagaacttat atctaggatc acccgcaaat 15540
tttgggggca cattcttctt tactccggga acagaaagtt gataaataag tttatccaga 15600
atctcaagtc cggctatctg atactagact tacaccagaa tatcttcgtt aagaatctat 15660
ccaagtcaga gaaacagatt attatgacgg ggggtttgaa acgtgagtgg gtttttaagg 15720
taacagtcaa ggagaccaaa gaatggtata agttagtcgg atacagtgcc ctgattaagg 15780
actaattggt tgaactccgg aaccctaatc ctgccctagg tggttaggca ttatttgcaa 15840
tatattaaag aaaactttga aaatacgaag tttctattcc cagctttgtc tggt 15894

<210> SEQ ID NO 3
<211> LENGTH: 19842
<212> TYPE: DNA
<213> ORGANISM: Artificial Sequence
<220> FEATURE:
<223> OTHER INFORMATION: Description of Artificial Sequence: Synthesized cDNA of recombinant measles virus vaccine for SARS-CoV-2

<400> SEQUENCE: 3
accaaacaaa gttgggtaag gatagttcaa tcaatgatca tcttctagtg cacttaggat 60
tcaagatcct attatcaggg acaagagcag gattagggat atccgagatg gccacacttt 120
taaggagctt agcattgttc aaaagaaaca aggacaaacc acccattaca tcaggatccg 180
gtggagccat cagaggaatc aaacacatta ttatagtacc aatccctgga gattcctcaa 240
ttaccactcg atccagactt ctggaccggt tggtcaggtt aattggaaac ccggatgtga 300
gcgggcccaa actaacaggg gcactaatag gtatattatc cttatttgtg gagtctccag 360
gtcaattgat tcagaggatc accgatgacc ctgacgttag cataaggctg ttagaggttg 420
tccagagtga ccagtcacaa tctggcctta ccttcgcatc aagaggtacc aacatggagg 480
atgaggcgga ccaatacttt tcacatgatg atccaattag tagtgatcaa tccaggttcg 540
gatggttcga gaacaaggaa atctcagata ttgaagtgca agaccctgag ggattcaaca 600
tgattctggg taccatccta gcccaaattt gggtcttgct cgcaaaggcg gttacggccc 660
cagacacggc agctgattcg gagctaagaa ggtggataaa gtacacccaa caaagaaggg 720
tagttggtga atttagattg gagagaaaat ggttggatgt ggtgaggaac aggattgccg 780
aggacctctc cttacgccga ttcatggtcg ctctaatcct ggatatcaag agaacacccg 840
gaaacaaacc caggattgct gaaatgatat gtgacattga tacatatatc gtagaggcag 900
gattagccag ttttatcctg actattaagt ttgggataga aactatgtat cctgctcttg 960
gactgcatga atttgctggt gagttatcca cacttgagtc cttgatgaac ctttaccagc 1020
aaatggggga aactgcaccc tacatggtaa tcctggagaa ctcaattcag aacaagttca 1080
gtgcaggatc ataccctctg ctctggagct atgccatggg agtaggagtg gaacttgaaa 1140
actccatggg aggtttgaac tttggccgat cttactttga tccagcatat tttagattag 1200
ggcaagagat ggtaaggagg tcagctggaa aggtcagttc cacattggca tctgaactcg 1260
gtatcactgc cgaggatgca aggcttgttt cagagattgc aatgcatact actgaggaca 1320
agatcagtag agcggttgga cccagacaag cccaagtatc atttctacac ggtgatcaaa 1380
gtgagaatga gctaccgaga ttgggggggca aggaagatag gagggtcaaa cagagtcgag 1440
gagaagccag ggagagctac agagaaaccg ggcccagcag agcaagtgat gcgagagctg 1500
cccatcttcc aaccggcaca cccctagaca ttgacactgc atcggagtcc agccaagatc 1560
cgcaggacag tcgaaggtca gctgacgccc tgcttaggct gcaagccatg gcaggaatct 1620
cggaagaaca aggctcagac acggacaccc ctatagtgta caatgacaga aatcttctag 1680
actagggccg gcctgccgag gaccagaaca acatccgcct accctccatc attgttataa 1740
aaaacttagg aaccaggtcc acacagccgc cagcccatca accatccact cccacgattg 1800
gagcagatgt tcgtctttct ggtgctcctt cctctggtca gttctcagtg tgtgaatctc 1860
accacaagaa cccagttgcc tcctgcttat accaacagct ttacacgggg tgtctattat 1920

-continued

```
cccgacaagg tgtttcgcag tagcgtacta cactctacac aggacctttt tctccccttc   1980
ttctccaatg tcacttggtt tcacgctatc cacgtctcag gcacaaatgg taccaagcgc   2040
tttgataatc ccgttctgcc ctttaatgat ggggtatatt ttgcctcaac cgaaaaatcc   2100
aacatcatcc ggggatggat ttttgggaca acccttgatt ccaagactca aagcctgctg   2160
atcgttaaca atgctaccaa cgttgtcatc aaagtatgcg agttccagtt ttgcaatgat   2220
ccatttctcg gcgtgtacta ccataagaac aataaatcat ggatggaatc cgaattccga   2280
gtgtactcct ctgctaacaa ctgcaccttt gaatacgtat ctcagccctt tctcatggat   2340
ctcgaaggaa agcagggaaa tttcaagaac ctccgggaat ttgtcttcaa gaatatagac   2400
gggtacttca aaatctactc taagcatacc cccatcaacc tggtgcgcga cctaccacaa   2460
ggcttcagtg ccctagagcc cctggtggac ttgcccatag gcattaatat cacgagattt   2520
cagacattat tggccctgca cagaagctat ctcacccctg gcgattccag tagtggatgg   2580
accgctggcg cagccgccta ttacgtggga tacttgcagc cacgaacttt cctactcaag   2640
tataatgaga acggaaccat aaccgatgca gtagattgtg ccttggatcc tctttctgag   2700
acaaaatgta cactgaagtc gttcacagtg gagaaaggga tctaccagac aagcaacttc   2760
agggttcaac cgactgagtc tatcgtcagg tttccaaata taaccaacct ttgtccgttt   2820
ggcgaagtgt tcaatgccac tagattcgcg tccgtctatg catggaatcg caaaaggatt   2880
tccaactgtg tggccgatta cagcgtgttg tacaattcag ccagcttcag cacctttaag   2940
tgctatggag tgtctccaac gaaactcaac gatctgtgtt tcacgaatgt gtacgccgat   3000
tcattcgtca ttcggggaga cgaagtcaga cagatagccc cagggcagac agggaaaatt   3060
gccgactata actacaaact gccagatgac ttcaccggtt gcgtgatagc ttggaattct   3120
aataacctcg acagcaaggt tggagggaac tacaattatc tgtaccggct gttccgtaag   3180
tcaaacctga aacccttga acgcgacatc tccacagaga tttaccaagc tggatccacc   3240
ccttgcaatg gggtagaggg attcaattgc tactttccgc tgcagtctta tgggtttcaa   3300
cccaccaatg gagtggggta ccagccctac cgagtggttg tcctgtcctt tgaattgttg   3360
catgcccccg cgaccgtgtg tggccccaag aagagtacaa atctcgttaa aaacaagtgc   3420
gtaaacttca actttaacgg tttgacgggg actggggtgc tgacggaatc aaacaagaaa   3480
ttcctgccgt tccagcagtt cgggagggac attgccgaca caaccgacgc tgtcagggat   3540
ccacagaccc tggagatctt ggacattaca ccttgctcct tcggcggcgt gagtgtaatc   3600
acacctggaa ctaacacgag taaccaggtt gccgtcctgt accaagacgt gaattgcacc   3660
gaggttccag ttgcgatcca cgcggatcag cttactccta catggcgagt gtatagtaca   3720
ggcagtaacg tattccagac tcgtgccggg tgtttaatag gggcagaaca cgtgaataac   3780
agttatgagt gtgacattcc gatcggcgct ggtatatgcg catcatacca aacccagact   3840
aactcaccta gaagagcccg ctccgtggcc agccagagca ttatcgccta tacgatgagc   3900
ctgggtgctg agaattccgt agcatattct aacaattcca ttgctattcc taccaacttt   3960
accatctctg ttaccactga gattctccca gtgtctatga ctaagacatc agtggactgc   4020
actatgtata tctgcggcga tagcactgag tgtagcaatt tgctcctgca atatggttca   4080
ttttgcaccc agcttaatag ggccctgaca ggaattgccg ttgagcagga caagaatact   4140
caggaggtct tcgctcaggt taagcagatc tacaagactc cgccaattaa ggacttcggc   4200
ggatttaact tcagccagat tctgccagac ccaagtaagc cctccaaaag gtcttttatc   4260
gaggatctgc tgttcaacaa agtgacactt gccgatgctg gctttatcaa acagtatgga   4320
```

```
gactgtctcg gtgatatagc agcacgggac ctcatctgcg cccagaagtt taacggactg   4380
accgtcctgc ctcctcttct gacagacgag atgattgctc agtacacttc ggcgctgctt   4440
gcaggtacta tcacaagcgg ctggacgttt ggtgccggag ccgcgctcca aattccattc   4500
gcaatgcaga tggcttatag attcaacggc ataggtgtca cccagaacgt gctgtacgaa   4560
aaccagaagc tcatagcgaa ccagtttaac tccgccatag ggaaaatcca ggattcgctc   4620
tccagtacag catccgcatt agggaaactg caggacgttg tgaatcagaa cgcccaagct   4680
cttaatacac tggtgaaaca attgtcatcc aatttcgggg caatcagctc tgtgcttaat   4740
gacatcctct cacggctgga taaagtcgaa gccgaagttc agattgatcg cttgattact   4800
ggtcggttac agtcactaca gacatatgtg acccagcagc tgattcgtgc tgccgagatt   4860
agggcatcgg ctaacctggc agctactaag atgtccgagt gcgtgcttgg ccaatcgaaa   4920
cgcgtggatt tctgtggcaa aggctatcat ctgatgagct tccctcaaag cgcgccccat   4980
ggcgtggtgt ttctgcacgt gacgtatgtc cccgcacagg agaagaattt cacaacagcc   5040
cccgcaatct gtcacgatgg caaggcacac tttcctcgag aaggggtttt cgtgagcaat   5100
ggcacccact ggttcgtgac ccagaggaac ttttatgagc cgcaaattat cactacggat   5160
aatacctttg tgagtggaaa ctgtgacgtg gtgattggaa tcgtcaacaa tactgtatac   5220
gaccccttac aacctgaact ggactctttc aaagaggaac tagacaagta ctttaagaac   5280
catacttctc cagacgtcga tttaggagac atttcaggca tcaatgccag cgtggtgaac   5340
atccagaagg agatcgatag actgaacgaa gtcgctaaga atttaaacga aagcctaata   5400
gacctgcaag agctgggcaa atacgagcag tacattaagt ggccatggta catctggttg   5460
ggcttcatcg ctggccttat cgccattgtt atggtcacca tcatgctctg ctgcatgact   5520
tcttgttgca gttgcttaaa agggtgttgc agctgtggca gctgctgtaa gttcgacgag   5580
gatgattccg agcccgtgct aaaaggtgtt aagctgcatt acacgtaata ataggccggc   5640
ctgccgagga ccagaacaac atccgcctac cctccatcat tgttataaaa aacttaggaa   5700
ccaggtccac acagccgcca gcccatcaac catccactcc cacgattgga gcagatggca   5760
gaagagcagg cacgccatgt caaaaacgga ctggaatgca tccgggctct caaggccgag   5820
cccatcggct cactggccat cgaggaagct atggcagcat ggtcagaaat atcagacaac   5880
ccaggacagg agcgagccac ctgcagggaa gagaaggcag gcagttcggg tctcagcaaa   5940
ccatgcctct cagcaattgg atcaactgaa ggcggtgcac ctcgcatccg cggtcaggga   6000
cctggagaga gcgatgacga cgctgaaact ttgggaatcc ccccaagaaa tctccaggca   6060
tcaagcactg ggctacagtg tcattatgtt tatgatcaca gcggtgaagc ggttaaggga   6120
atccaagatg ctgactctat catggttcaa tcaggccttg atggtgatag caccctctca   6180
ggaggagaca atgaatctga aaacagcgat gtggatattg gcgaacctga taccgaggga   6240
tatgctatca ctgaccgggg atctgctccc atctctatgg ggttcagggc ttctgatgtt   6300
gaaactgcag aaggagggga gatccacgag ctcctgagac tccaatccag aggcaacaac   6360
tttccgaagc ttgggaaaac tctcaatgtt cctccgcccc cggaccccgg tagggccagc   6420
acttccggga cacccattaa aaagggcaca gacgcgagat tagcctcatt tggaacggag   6480
atcgcgtctt cattgacagg tggtgcaacc caatgtgctc gaaagtcacc ctcggaacca   6540
tcagggccag gtgcacctgc ggggaacgtc cccgagtgtg tgagcaatgc cgcactgata   6600
caggagtgga cacccgaatc tggcaccaca atctccccga gatcccagaa taatgaagaa   6660
```

gggggagacc attatgatga tgagctgttc tctgatgtcc aagatattaa aacagccttg 6720
gccaaaatac acgaggataa tcagaagata atctccaagc tagaatcact gctgttattg 6780
aagggagaag ttgagtcaat taagaagcag atcaacaggc aaaatatcag catatccacc 6840
ctggaaggac acctctcaag catcatgatc gccattcctg gacttgggaa ggatcccaac 6900
gaccccactg cagatgtcga aatcaatccc gacttgaaac ccatcatagg cagagattca 6960
ggccgagcac tggccgaagt tctcaagaaa cccgttgcca gccgacaact ccaaggaatg 7020
acaaatggac ggaccagttc cagaggacag ctgctgaagg aatttcagct aaagccgatc 7080
gggaaaaaga tgagctcagc cgtcgggttt gttcctgaca ccggccctgc atcacgcagt 7140
gtaatccgct ccattataaa atccagccgg ctagaggagg atcggaagcg ttacctgatg 7200
actctccttg atgatatcaa aggagccaat gatcttgcca agttccacca gatgctggtg 7260
aagataataa tgaagtagct acagctcaac ttacctgcca accccatgcc agtcgaccca 7320
actagtacaa cctaaatcca ttataaaaaa cttaggagca aagtgattgc ctcccaagtt 7380
ccacaatgac agagatctac gacttcgaca agtcggcatg ggacatcaaa gggtcgatcg 7440
ctccgataca acccaccacc tacagtgatg gcaggctggt gccccaggtc agagtcatag 7500
atcctggtct aggcgacagg aaggatgaat gctttatgta catgtttctg ctgggggttg 7560
ttgaggacag cgattcccta gggcctccaa tcgggcgagc atttgggtcc ctgcccttag 7620
gtgttggcag atccacagca aagcccgaaa aactcctcaa agaggccact gagcttgaca 7680
tagttgttag acgtacagca gggctcaatg aaaaactggt gttctacaac aacaccccac 7740
taactctcct cacaccttgg agaaaggtcc taacaacagg gagtgtcttc aacgcaaacc 7800
aagtgtgcaa tgcggttaat ctgataccgc tcgatacccc gcagaggttc cgtgttgttt 7860
atatgagcat cacccgtctt tcggataacg ggtattacac cgttcctgga agaatgctgg 7920
aattcagatc ggtcaatgca gtggccttca acctgctggt gacccttagg attgacaagg 7980
cgataggccc tgggaagatc atcgacaata cagagcaact tcctgaggca acatttatgg 8040
tccacatcgg gaacttcagg agaaagaaga gtgaagtcta ctctgccgat tattgcaaaa 8100
tgaaaatcga aaagatgggc ctggtttttg cacttggtgg gatagggggc accagtcttc 8160
acattagaag cacaggcaaa atgagcaaga ctctccatgc acaactcggg ttcaagaaga 8220
ccttatgtta cccgctgatg gatatcaatg aagaccttaa tcgattactc tggaggagca 8280
gatgcaagat agtaagaatc caggcagttt tgcagccatc agttcctcaa gaattccgca 8340
tttacgacga cgtgatcata aatgatgacc aaggactatt caaagttctg tagaccgtag 8400
tgcccagcaa tgcccgaaaa cgacccccct cacaatgaca gccagaaggc ccggacaaaa 8460
aagccccctc cgaaagactc cacggaccaa gcgagaggcc agccagcagc cgacggcaag 8520
cgcgaacacc aggcggcccc agcacagaac agccctgaca caaggccacc accagccacc 8580
ccaatctgca tcctcctcgt gggacccccg aggaccaacc cccaaggctg cccccgatcc 8640
aaaccaccaa ccgcatcccc accacccccg ggaaagaaac cccccagcaat tggaaggccc 8700
ctccccctct tcctcaacac aagaactcca caaccgaacc gcacaagcga ccgaggtgac 8760
ccaaccgcag gcatccgact ccctagacag atcctctctc cccggcaaac taaacaaaac 8820
ttagggccaa ggaacataca cacccaacag aacccagacc ccggcccacg gcgccgcgcc 8880
cccaaccccc gacaaccaga gggagccccc aaccaatccc gccggctccc ccggtgccca 8940
caggcaggga caccaacccc cgaacagacc cagcacccaa ccatcgacaa tccaagacgg 9000
gggggccccc ccaaaaaaag gcccccaggg gccgacagcc agcaccgcga ggaagcccac 9060

```
ccaccccaca cacgaccacg gcaaccaaac cagaacccag accaccctgg gccaccagct   9120
cccagactcg gccatcaccc cgcagaaagg aaaggccaca acccgcgcac cccagccccg   9180
atccggcggg gagccaccca acccgaacca gcacccaaga gcgatccccg aaggaccccc   9240
gaaccgcaaa ggacatcagt atcccacagc ctctccaagt cccccggtct cctcctcttc   9300
tcgaagggac caaaagatca atccaccaca cccgacgaca ctcaactccc cacccctaaa   9360
ggagacaccg ggaatcccag aatcaagact catccaatgt ccatcatggg tctcaaggtg   9420
aacgtctctg ccatattcat ggcagtactg ttaactctcc aaacacccac cggtcaaatc   9480
cattggggca atctctctaa gataggggtg gtaggaatag gaagtgcaag ctacaaagtt   9540
atgactcgtt ccagccatca atcattagtc ataaaattaa tgcccaatat aactctcctc   9600
aataactgca cgagggtaga gattgcagaa tacaggagac tactgagaac agttttggaa   9660
ccaattagag atgcacttaa tgcagtgacc cagaatataa gaccggttca gagtgtagct   9720
tcaagtagga gacacaagag atttgcggga gtagtcctgg caggtgcggc cctaggcgtt   9780
gccacagctg ctcagataac agccggcatt gcacttcacc agtccatgct gaactctcaa   9840
gccatcgaca atctgagagc gagcctggaa actactaatc aggcaattga ggcaatcaga   9900
caagcagggc aggagatgat attggctgtt cagggtgtcc aagactacat caataatgag   9960
ctgataccgt ctatgaacca actatcttgt gatttaatcg gccagaagct cgggctcaaa  10020
ttgctcagat actatacaga aatcctgtca ttatttggcc ccagcttacg ggaccccata  10080
tctgcggaga tatctatcca ggctttgagc tatgcgcttg gaggagacat caataaggtg  10140
ttagaaaagc tcggatacag tggaggtgat ttactgggca tcttagagag cagaggaata  10200
aaggcccgga taactcacgt cgacacagag tcctacttca ttgtcctcag tatagcctat  10260
ccgacgctgt ccgagattaa gggggtgatt gtccaccggc tagagggggt ctcgtacaac  10320
ataggctctc aagagtggta taccactgtg cccaagtatg ttgcaaccca agggtacctt  10380
atctcgaatt ttgatgagtc atcgtgtact ttcatgccag aggggactgt gtgcagccaa  10440
aatgccttgt acccgatgag tcctctgctc caagaatgcc tccgggggtc caccaagtcc  10500
tgtgctcgta cactcgtatc cgggtctttt gggaaccggt tcattttatc acaagggaac  10560
ctaatagcca attgtgcatc aatcctttgc aagtgttaca caacaggaac gatcattaat  10620
caagaccctg acaagatcct aacatacatt gctgccgatc actgcccggt agtcgaggtg  10680
aacggcgtga ccatccaagt cgggagcagg aggtatccag acgctgtgta cttgcacaga  10740
attgacctcg gtcctcccat atcattggag aggttggacg tagggacaaa tctggggaat  10800
gcaattgcta agttggagga tgccaaggaa ttgttggagt catcggacca gatattgagg  10860
agtatgaaag gtttatcgag cactagcata gtctacatcc tgattgcagt gtgtcttgga  10920
gggttgatag ggatccccgc tttaatatgt tgctgcaggg ggcgttgtaa caaaaaggga  10980
gaacaagttg gtatgtcaag accaggccta aagcctgatc ttacgggaac atcaaaatcc  11040
tatgtaaggt cgctctgatc ctctacaact cttgaaacac aaatgtccca caagtctcct  11100
cttcgtcatc aagcaaccac cgcacccagc atcaagccca cctgaaatta tctccggttt  11160
ccctctggcc gaacaatatc ggtagttaat taaaacttag ggtgcaagat catccacaat  11220
gtcaccacaa cgagaccgga taaatgcctt ctacaaagat aacccccatc ccaagggaag  11280
taggatagtc attaacagag aacatcttat gattgataga ccttatgttt tgctggctgt  11340
tctgtttgtc atgtttctga gcttgatcgg gttgctagcc attgcaggca ttagacttca  11400
```

-continued

```
tcgggcagcc atctacaccg cagagatcca taaaagcctc agcaccaatc tagatgtaac  11460
taactcaatc gagcatcagg tcaaggacgt gctgacacca ctcttcaaaa tcatcggtga  11520
tgaagtgggc ctgaggacac ctcagagatt cactgaccta gtgaaattca tctctgacaa  11580
gattaaattc cttaatccgg atagggagta cgacttcaga gatctcactt ggtgtatcaa  11640
cccgccagag agaatcaaat tggattatga tcaatactgt gcagatgtgg ctgctgaaga  11700
gctcatgaat gcattggtga actcaactct actggagacc agaacaacca atcagttcct  11760
agctgtctca aagggaaact gctcagggcc cactacaatc agaggtcaat tctcaaacat  11820
gtcgctgtcc ctgttagact tgtatttagg tcgaggttac aatgtgtcat ctatagtcac  11880
tatgacatcc cagggaatgt atgggggaac ttacctagtg gaaaagccta atctgagcag  11940
caaaaggtca gagttgtcac aactgagcat gtaccgagtg tttgaagtag gtgttatcag  12000
aaatccgggt ttgggggctc cggtgttcca tatgacaaac tatcttgagc aaccagtcag  12060
taatgatctc agcaactgta tggtggcttt gggggagctc aaactcgcag ccctttgtca  12120
cggggaagat tctatcacaa ttccctatca gggatcaggg aaaggtgtca gcttccagct  12180
cgtcaagcta ggtgtctgga aatccccaac cgacatgcaa tcctgggtcc ccttatcaac  12240
ggatgatcca gtgatagaca ggctttacct ctcatctcac agaggtgtta tcgctgacaa  12300
ccaagcaaaa tgggctgtcc cgacaacacg aacagatgac aagttgcgaa tggagacatg  12360
cttccaacag gcgtgtaagg gtaaaatcca agcactctgc gagaatcccg agtgggcacc  12420
attgaaggat aacaggattc cttcatacgg ggtcttgtct gttgatctga gtctgacagt  12480
tgagcttaaa atcaaaattg cttcgggatt cgggccattg atcacacacg gttcagggat  12540
ggacctatac aaatccaacc acaacaatgt gtattggctg actatcccgc caatgaagaa  12600
cctagcctta ggtgtaatca acacattgga gtggataccg agattcaagg ttagtcccta  12660
cctcttcact gtcccaatta aggaagcagg cggagactgc catgccccaa catacctacc  12720
tgcggaggtg gatggtgatg tcaaactcag ttccaatctg gtgattctac ctggtcaaga  12780
tctccaatat gttttggcaa cctacgatac ttccagggtt gaacatgctg tggtttatta  12840
cgtttacagc ccaagccgct cattttctta cttttatcct tttaggttgc ctataaaggg  12900
ggtccccatc gaattacaag tggaatgctt cacatgggac caaaaactct ggtgccgtca  12960
cttctgtgtg cttgcggact cagaatctgg tggacatatc actcactctg ggatggtggg  13020
catgggagtc agctgcacag tcacccggga agatggaacc aatcgcagat agggctgcta  13080
gtgaaccaat cacatgatgt cacccagaca tcaggcatac ccactagtgt gaaatagaca  13140
tcagaattaa gaaaaacgta gggtccaagt ggttccccgt tatggactcg ctatctgtca  13200
accagatctt ataccctgaa gttcacctag atagcccgat agttaccaat aagatagtag  13260
ccatcctgga gtatgctcga gtccctcacg cttacagcct ggaggaccct acactgtgtc  13320
agaacatcaa gcaccgccta aaaaacggat tttccaacca aatgattata aacaatgtgg  13380
aagttgggaa tgtcatcaag tccaagctta ggagttatcc ggcccactct catattccat  13440
atccaaattg taatcaggat ttatttaaca tagaagacaa agagtcaacg aggaagatcc  13500
gtgaactcct caaaaagggg aattcgctgt actccaaagt cagtgataag gttttccaat  13560
gcttaaggga cactaactca cggcttggcc taggctccga attgagggag gacatcaagg  13620
agaaagttat taacttggga gtttacatgc acagctccca gtggtttgag ccctttctgt  13680
tttggtttac agtcaagact gagatgaggt cagtgattaa atcacaaacc catacttgcc  13740
ataggaggag acacacacct gtattcttca ctggtagttc agttgagttg ctaatctctc  13800
```

gtgaccttgt tgctataatc agtaaagagt ctcaacatgt atattacctg acatttgaac 13860
tggttttgat gtattgtgat gtcatagagg ggaggttaat gacagagacc gctatgacta 13920
ttgatgctag gtatacagag cttctaggaa gagtcagata catgtggaaa ctgatagatg 13980
gtttcttccc tgcactcggg aatccaactt atcaaattgt agccatgctg gagcctcttt 14040
cacttgctta cctgcagctg agggatataa cagtagaact cagaggtgct ttccttaacc 14100
actgctttac tgaaatacat gatgttcttg accaaaacgg gttttctgat gaaggtactt 14160
atcatgagtt aattgaagct ctagattaca ttttcataac tgatgacata catctgacag 14220
gggagatttt ctcatttttc agaagtttcg gccaccccag acttgaagca gtaacggctg 14280
ctgaaaatgt taggaaatac atgaatcagc ctaaagtcat tgtgtatgag actctgatga 14340
aaggtcatgc catattttgt ggaatcataa tcaacggcta tcgtgacagg cacggaggca 14400
gttggccacc gctgaccctc cccctgcatg ctgcagacac aatccggaat gctcaagctt 14460
caggtgatgg gttaacacat gagcagtgcg ttgataactg gaaatctttt gctggagtga 14520
aatttggctg ctttatgcct cttagcctgg atagtgatct gacaatgtac ctaaaggaca 14580
aggcacttgc tgctctccaa agggaatggg attcagttta cccgaaagag ttcctgcgtt 14640
acgaccctcc caagggaacc gggtcacgga ggcttgtaga tgttttcctt aatgattcga 14700
gctttgaccc atatgatgtg ataatgtatg ttgtaagtgg agcttacctc catgaccctg 14760
agttcaacct gtcttacagc ctgaaagaaa aggagatcaa ggaaacaggt agactttttg 14820
ctaaaatgac ttacaaaatg agggcatgcc aagtgattgc tgaaaatcta atctcaaacg 14880
ggattggcaa atattttaag gacaatggga tggccaagga tgagcacgat ttgactaagg 14940
cactccacac tctagctgtc tcaggagtcc ccaaagatct caaagaaagt cacaggggggg 15000
ggccagtctt aaaaacctac tcccgaagcc cagtccacac aagtaccagg aacgtgagag 15060
cagcaaaagg gtttataggg ttccctcaag taattcggca ggaccaagac actgatcatc 15120
cggagaatat ggaagcttac gagacagtca gtgcatttat cacgactgat ctcaagaagt 15180
actgccttaa ttggagatat gagaccatca gcttgtttgc acagaggcta aatgagattt 15240
acggattgcc ctcatttttc cagtggctgc ataagaggct tgagacctct gtcctgtatg 15300
taagtgaccc tcattgcccc cccgaccttg acgcccatat cccgttatat aaagtcccca 15360
atgatcaaat cttcattaag taccctatgg gaggtataga agggtattgt cagaagctgt 15420
ggaccatcag caccattccc tatctatacc tggctgctta tgagagcgga gtaaggattg 15480
cttcgttagt gcaaggggac aatcagacca tagccgtaac aaaaagggta cccagcacat 15540
ggccctacaa ccttaagaaa cgggaagctg ctagagtaac tagagattac tttgtaattc 15600
ttaggcaaag gctacatgat attggccatc acctcaaggc aaatgagaca attgtttcat 15660
cacatttttt tgtctattca aaaggaatat attatgatgg gctacttgtg tcccaatcac 15720
tcaagagcat cgcaagatgt gtattctggt cagagactat agttgatgaa acaagggcag 15780
catgcagtaa tattgctaca acaatggcta aaagcatcga gagaggttat gaccgttacc 15840
ttgcatattc cctgaacgtc ctaaaagtga tacagcaaat tctgatctct cttggcttca 15900
caatcaattc aaccatgacc cgggatgtag tcatacccct cctcacaaac aacgacctct 15960
taataaggat ggcactgttg cccgctccta ttgggggggat gaattatctg aatatgagca 16020
ggctgtttgt cagaaacatc ggtgatccag taacatcatc aattgctgat ctcaagagaa 16080
tgattctcgc ctcactaatg cctgaagaga ccctccatca ggtaatgaca caacaaccgg 16140

-continued

```
gggactcttc attcctagac tgggctagcg acccttactc agcaaatctt gtatgtgtcc  16200
agagcatcac tagactcctc aagaacataa ctgcaaggtt tgtcctgatc catagtccaa  16260
acccaatgtt aaaaggatta ttccatgatg acagtaaaga agaggacgag ggactggcgg  16320
cattcctcat ggacaggcat attatagtac ctagggcagc tcatgaaatc ctggatcata  16380
gtgtcacagg ggcaagagag tctattgcag gcatgctgga taccacaaaa ggcttgattc  16440
gagccagcat gaggaagggg ggtttaacct ctcgagtgat aaccagattg tccaattatg  16500
actatgaaca attcagagca gggatggtgc tattgacagg aagaaagaga aatgtcctca  16560
ttgacaaaga gtcatgttca gtgcagctgg cgagagctct aagaagccat atgtgggcga  16620
ggctagctcg aggacggcct atttacggcc ttgaggtccc tgatgtacta gaatctatgc  16680
gaggccacct tattcggcgt catgagacat gtgtcatctg cgagtgtgga tcagtcaact  16740
acggatggtt ttttgtcccc tcgggttgcc aactggatga tattgacaag gaaacatcat  16800
ccttgagagt cccatatatt ggttctacca ctgatgagag aacagacatg aagcttgcct  16860
tcgtaagagc cccaagtcga tccttgcgat ctgctgttag aatagcaaca gtgtactcat  16920
gggcttacgg tgatgatgat agctcttgga acgaagcctg gttgttggct aggcaaaggg  16980
ccaatgtgag cctggaggag ctaagggtga tcactcccat ctcaacttcg actaatttag  17040
cgcataggtt gagggatcgt agcactcaag tgaaatactc aggtacatcc cttgtccgag  17100
tggcgaggta taccacaatc tccaacgaca atctctcatt tgtcatatca gataagaagg  17160
ttgatactaa ctttatatac caacaaggaa tgcttctagg gttgggtgtt ttagaaacat  17220
tgtttcgact cgagaaagat accggatcat ctaacacggt attacatctt cacgtcgaaa  17280
cagattgttg cgtgatcccg atgatagatc atcccaggat acccagctcc cgcaagctag  17340
agctgagggc agagctatgt accaacccat tgatatatga taatgcacct ttaattgaca  17400
gagatgcaac aaggctatac acccagagcc ataggaggca ccttgtggaa tttgttacat  17460
ggtccacacc ccaactatat cacattttag ctaagtccac agcactatct atgattgacc  17520
tggtaacaaa atttgagaag gaccatatga atgaaatttc agctctcata ggggatgacg  17580
atatcaatag tttcataact gagtttctgc tcatagagcc aagattattc actatctact  17640
tgggccagtg tgcggccatc aattgggcat ttgatgtaca ttatcataga ccatcaggga  17700
aatatcagat gggtgagctg ttgtcatcgt tcctttctag aatgagcaaa ggagtgttta  17760
aggtgcttgt caatgctcta agccacccaa agatctacaa gaaattctgg cattgtggta  17820
ttatagagcc tatccatggt ccttcacttg atgctcaaaa cttgcacaca actgtgtgca  17880
acatggttta cacatgctat atgacctacc tcgacctgtt gttgaatgaa gagttagaag  17940
agttcacatt tctcttgtgt gaaagcgacg aggatgtagt accggacaga ttcgacaaca  18000
tccaggcaaa acacttatgt gttctggcag atttgtactg tcaaccaggg acctgcccac  18060
caattcaagg tctaagaccg gtagagaaat gtgcagttct aaccgaccat atcaaggcag  18120
aggctatgtt atctccagca ggatcttcgt ggaacataaa tccaattatt gtagaccatt  18180
actcatgctc cctgacttat ctccggcgag gatcgatcaa acagataaga ttgagagttg  18240
atccaggatt cattttcgac gccctcgctg aggtaaatgt cagtcagcca aagatcggca  18300
gcaacaacat ctcaaatatg agcatcaagg ctttcagacc cccacacgat gatgttgcaa  18360
aattgctcaa agatatcaac acaagcaagc acaatcttcc catttcaggg ggcaatctcg  18420
ccaattatga aatccatgct ttccgcagaa tcgggttgaa ctcatctgct tgctacaaag  18480
ctgttgagat atcaacatta attaggagat gccttgagcc aggggaggac ggcttgttct  18540
```

tgggtgaggg atcgggttct atgttgatca cttataagga gatacttaaa ctaagcaagt 18600
gcttctataa tagtggggtt tccgccaatt ctagatctgg tcaaagggaa ttagcaccct 18660
atccctccga agttggcctt gtcgaacaca gaatgggagt aggtaatatt gtcaaagtgc 18720
tctttaacgg gaggcccgaa gtcacgtggg taggcagtgt agattgcttc aatttcatag 18780
ttagtaatat ccctacctct agtgtggggt ttatccattc agatatagag accttgcctg 18840
acaaagatac tatagagaag ctagaggaat tggcagccat cttatcgatg gctctgctcc 18900
tgggcaaaat aggatcaata ctggtgatta agcttatgcc tttcagcggg gattttgttc 18960
agggatttat aagttatgta gggtctcatt atagagaagt gaaccttgta taccctagat 19020
acagcaactt catatctact gaatcttatt tggttatgac agatctcaag gctaaccggc 19080
taatgaatcc tgaaaagatt aagcagcaga taattgaatc atctgtgagg acttcacctg 19140
gacttatagg tcacatccta tccattaagc aactaagctg catacaagca attgtgggag 19200
acgcagttag tagaggtgat atcaatccta ctctgaaaaa acttacacct atagagcagg 19260
tgctgatcaa ttgcgggttg gcaattaacg gacctaagct gtgcaaagaa ttgatccacc 19320
atgatgttgc ctcagggcaa gatggattgc ttaattctat actcatcctc tacagggagt 19380
tggcaagatt caaagacaac caaagaagtc aacaagggat gttccacgct taccccgtat 19440
tggtaagtag caggcaacga gaacttatat ctaggatcac ccgcaaattt tgggggcaca 19500
ttcttcttta ctccgggaac agaaagttga taaataagtt tatccagaat ctcaagtccg 19560
gctatctgat actagactta caccagaata tcttcgttaa gaatctatcc aagtcagaga 19620
aacagattat tatgacgggg ggtttgaaac gtgagtgggt ttttaaggta acagtcaagg 19680
agaccaaaga atggtataag ttagtcggat acagtgccct gattaaggac taattggttg 19740
aactccggaa ccctaatcct gccctaggtg gttaggcatt atttgcaata tattaaagaa 19800
aactttgaaa atacgaagtt tctattccca gctttgtctg gt 19842

<210> SEQ ID NO 4
<211> LENGTH: 3822
<212> TYPE: DNA
<213> ORGANISM: Artificial Sequence
<220> FEATURE:
<223> OTHER INFORMATION: Description of Artificial Sequence: Synthesized
recombinant cDNA of SARS-CoV-2 spike protein

<400> SEQUENCE: 4
atgttcgtct ttctggtgct ccttcctctg gtcagttctc agtgtgtgaa tctcaccaca 60
agaacccagt tgcctcctgc ttataccaac agctttacac ggggtgtcta ttatcccgac 120
aaggtgtttc gcagtagcgt actacactct acacaggacc tttttctccc cttcttctcc 180
aatgtcactt ggtttcacgc tatccacgtc tcaggcacaa atggtaccaa gcgctttgat 240
aatcccgttc tgccctttaa tgatggggta tattttgcct caaccgaaaa atccaacatc 300
atccggggat ggatttttgg gacaaccctt gattccaaga ctcaaagcct gctgatcgtt 360
aacaatgcta ccaacgttgt catcaaagta tgcgagttcc agttttgcaa tgatccattt 420
ctcggcgtgt actaccataa gaacaataaa tcatggatgg aatccgaatt ccgagtgtac 480
tcctctgcta acaactgcac ctttgaatac gtatctcagc cctttctcat ggatctcgaa 540
ggaaagcagg gaaatttcaa gaacctccgg gaatttgtct tcaagaatat agacgggtac 600
ttcaaaatct actctaagca tacccccatc aacctggtgc gcgacctacc acaaggcttc 660
agtgccctag agcccctggt ggacttgccc ataggcatta atatcacgag atttcagaca 720
ttattggccc tgcacagaag ctatctcacc cctggcgatt ccagtagtgg atggaccgct 780
ggcgcagccg cctattacgt gggatacttg cagccacgaa ctttcctact caagtataat 840
gagaacggaa ccataaccga tgcagtagat tgtgccttgg atcctctttc tgagacaaaa 900
tgtacactga agtcgttcac agtggagaaa gggatctacc agacaagcaa cttcagggtt 960
caaccgactg agtctatcgt caggtttcca aatataacca acctttgtcc gtttggcgaa 1020
gtgttcaatg ccactagatt cgcgtccgtc tatgcatgga atcgcaaaag gatttccaac 1080
tgtgtggccg attacagcgt gttgtacaat tcagccagct tcagcacctt taagtgctat 1140
ggagtgtctc caacgaaact caacgatctg tgtttcacga atgtgtacgc cgattcattc 1200
gtcattcggg gagacgaagt cagacagata gccccagggc agacagggaa aattgccgac 1260
tataactaca aactgccaga tgacttcacc ggttgcgtga tagcttggaa ttctaataac 1320
ctcgacagca aggttggagg gaactacaat tatctgtacc ggctgttccg taagtcaaac 1380
ctgaaaccct ttgaacgcga catctccaca gagatttacc aagctggatc caccccttgc 1440
aatggggtag agggattcaa ttgctacttt ccgctgcagt cttatgggtt tcaacccacc 1500
aatggagtgg ggtaccagcc ctaccgagtg gttgtcctgt cctttgaatt gttgcatgcc 1560
cccgcgaccg tgtgtggccc caagaagagt acaaatctcg ttaaaaacaa gtgcgtaaac 1620
ttcaacttta acggtttgac ggggactggg gtgctgacgg aatcaaacaa gaaattcctg 1680
ccgttccagc agttcgggag ggacattgcc gacacaaccg acgctgtcag ggatccacag 1740
accctggaga tcttggacat tacaccttgc tccttcggcg gcgtgagtgt aatcacacct 1800
ggaactaaca cgagtaacca ggttgccgtc ctgtaccaag acgtgaattg caccgaggtt 1860
ccagttgcga tccacgcgga tcagcttact cctacatggc gagtgtatag tacaggcagt 1920
aacgtattcc agactcgtgc cgggtgttta ataggggcag aacacgtgaa taacagttat 1980
gagtgtgaca ttccgatcgg cgctggtata tgcgcatcat accaaaccca gactaactca 2040
cctagaagag cccgctccgt ggccagccag agcattatcg cctatacgat gagcctgggt 2100
gctgagaatt ccgtagcata ttctaacaat tccattgcta ttcctaccaa ctttaccatc 2160
tctgttacca ctgagattct cccagtgtct atgactaaga catcagtgga ctgcactatg 2220
tatatctgcg gcgatagcac tgagtgtagc aatttgctcc tgcaatatgg ttcattttgc 2280
acccagctta atagggccct gacaggaatt gccgttgagc aggacaagaa tactcaggag 2340
gtcttcgctc aggttaagca gatctacaag actccgccaa ttaaggactt cggcggattt 2400
aacttcagcc agattctgcc agacccaagt aagccctcca aaaggtcttt tatcgaggat 2460
ctgctgttca acaaagtgac acttgccgat gctggcttta tcaaacagta tggagactgt 2520
ctcggtgata tagcagcacg ggacctcatc tgcgcccaga agtttaacgg actgaccgtc 2580
ctgcctcctc ttctgacaga cgagatgatt gctcagtaca cttcggcgct gcttgcaggt 2640
actatcacaa gcggctggac gtttggtgcc ggagccgcgc tccaaattcc attcgcaatg 2700
cagatggctt atagattcaa cggcataggt gtcacccaga acgtgctgta cgaaaaccag 2760
aagctcatag cgaaccagtt taactccgcc atagggaaaa tccaggattc gctctccagt 2820
acagcatccg cattagggaa actgcaggac gttgtgaatc agaacgccca agctcttaat 2880
acactggtga aacaattgtc atccaatttc ggggcaatca gctctgtgct taatgacatc 2940
ctctcacggc tggataaagt cgaagccgaa gttcagattg atcgcttgat tactggtcgg 3000
ttacagtcac tacagacata tgtgacccag cagctgattc gtgctgccga gattagggca 3060

-continued

```
tcggctaacc tggcagctac taagatgtcc gagtgcgtgc ttggccaatc gaaacgcgtg   3120

gatttctgtg gcaaaggcta tcatctgatg agcttccctc aaagcgcgcc ccatggcgtg   3180

gtgtttctgc acgtgacgta tgtccccgca caggagaaga atttcacaac agcccccgca   3240

atctgtcacg atggcaaggc acactttcct cgagaagggg ttttcgtgag caatggcacc   3300

cactggttcg tgacccagag gaacttttat gagccgcaaa ttatcactac ggataatacc   3360

tttgtgagtg gaaactgtga cgtggtgatt ggaatcgtca acaatactgt atacgacccc   3420

ttacaacctg aactggactc tttcaaagag gaactagaca agtactttaa gaaccatact   3480

tctccagacg tcgatttagg agacatttca ggcatcaatg ccagcgtggt gaacatccag   3540

aaggagatcg atagactgaa cgaagtcgct aagaatttaa acgaaagcct aatagacctg   3600

caagagctgg gcaaatacga gcagtacatt aagtggccat ggtacatctg gttgggcttc   3660

atcgctggcc ttatcgccat tgttatggtc accatcatgc tctgctgcat gacttcttgt   3720

tgcagttgct taaaagggtg ttgcagctgt ggcagctgct gtaagttcga cgaggatgat   3780

tccgagcccg tgctaaaagg tgttaagctg cattacacgt aa                       3822
```

RECOMBINANT MEASLES VIRUS

Priority is claimed on Japanese Patent Application No. 2021-041015, filed Mar. 15, 2021, the content of which is incorporated herein by reference.

REFERENCE TO A SEQUENCE LISTING SUBMITTED ELECTRONICALLY

The official copy of the sequence listing is submitted electronically via Patent Center as an txt formatted sequence listing with a file name 16922400101RevisedSequenceListing, created on Sep. 13, 2023, and having a size of 68.3 bytes. The sequence listing contained in this txt formatted document is part of the specification and is herein incorporated by reference in its entirety.

BACKGROUND OF THE INVENTION

Technical Field

The present invention relates to a recombinant measles virus useful as a vaccine against a novel coronavirus infectious disease (COVID-19).

Background Art

COVID-19 is an infectious disease caused by a novel coronavirus, Severe Acute Respiratory Syndrome Coronavirus 2 (SARS-COV-2), as a causative pathogen. Coronaviruses invade host cells by a spike glycoprotein interacting with an angiotensin-converting enzyme of a receptor on the host cell surface.

COVID-19 has caused a pandemic and has become a global threat. Since the first infection was reported in December 2019, the number of infected individuals and the number of deaths have been increasing, and there is no sign that the number of cases may decrease. To end this pandemic, the development of therapeutic drugs or vaccines is of utmost importance, and there is a high demand for development of excellent vaccines worldwide. In addition, vaccines developed in each country are preferentially supplied to their own nation, and therefore, there is a need for Japan to develop its own vaccines.

Vaccines are broadly classified into live vaccines and inactivated vaccines. Many of the vaccines against COVID-19 which are currently being developed in various countries include the so-called inactivated vaccines, such as an inactivated virus, a SARS-COV-2 protein, and a nucleic acid (mRNA and DNA) for expressing the protein in a human body, and are mainly antigen-induced vaccines that induce humoral immunity. These inactivated vaccines have a short duration of immunity and are required to be administered frequently, and a large amount of preparations thereof need to be prepared. In addition, in COVID-19, antibody-dependent enhancement (ADE) is suggested to occur, and there is also a concern about the increasing severity of side effects caused by a large amount of antibodies being induced by frequent administration.

On the other hand, measles is caused by measles viruses classified under the family Paramyxoviridae, genus Morbillivirus. A hematoaggregin (H) protein and a fusion (F) protein are present in the external envelope of a measles virus, while in the internal capsid, a nucleocapsid (N) protein, a phosphoprotein (P), a large (L) protein, and a matrix (M) protein are present along with a helical negative RNA genome. The measles virus genome has, at both ends, a leader sequence and a trailer sequence involved in the replication of the virus, and genes encoding N, P, M, F, H, and L proteins are present in order from the 3' end, between the leader sequence and the trailer sequence. From the P gene region, not only the P protein but also the V protein and the C protein are translated.

Measles is an acute systemic infectious disease and may cause serious diseases such as pneumonia and encephalitis. The measles virus is highly infectious and infects through various routes such as airborne infection, droplet infection, and contact infection. For measles, there is no fundamental therapeutic drug, and vaccination is the most effective prophylactic method. As a vaccine against the measles, a live attenuated vaccine obtained by passaging a measles virus in a cell culture to weaken its virulence is used.

The live measles vaccine has excellent characteristics such as induction of strong cellular immunity and exhibition of extremely long immunity persistence referred to as permanent immunity. Furthermore, the live measles vaccine has been used all over the world for 50 years or longer, and its safety in humans has also been confirmed. Therefore, live vaccines against other diseases have been developed by using a genetic recombinant virus vector in which genes of microorganisms causing other diseases and the like are inserted into a genomic RNA of an attenuated measles strain virus useful as the measles vaccine. For example, a recombinant measles virus obtained by inserting an F gene or a G gene encoding a membrane protein of a Nipah virus into a measles virus genome functions as a bivalent vaccine against both measles and Nipah virus infectious disease (Patent Document 1). In addition, a recombinant measles virus obtained by inserting a gene of a protein of a malaria parasite into a measles virus genome functions as a bivalent vaccine against both measles and malaria infectious disease (Patent Document 2).

PATENT DOCUMENTS

Patent Document 1

Japanese Unexamined Patent Application, First Publication No. 2010-115154 Patent Document 2

Japanese Unexamined Patent Application, First Publication No. 2010-099041

Non-Patent Documents

Non-Patent Document 1

Rota et al, Virus Research, 1994, Vol. 31 (3), p. 317-330.

SUMMARY OF THE INVENTION

Technical Problem

A main object of the present invention is to provide a recombinant measles virus useful as a live vaccine against COVID-19, and a vector used for production of the recombinant measles virus.

Solution to Problem

The present inventors have conducted extensive studies, and as a result, they have found that a recombinant measles virus in which a gene encoding a spike protein of SARS-CoV-2 or a partial protein thereof is inserted into a cDNA of a measles virus genome is useful as a live vaccine against COVID-19, leading to completion of the present invention.

The recombinant measles virus and the like according to the present invention are as follows.

1. A recombinant measles virus, including a gene encoding a protein of coronavirus SARS-COV-2 or a partial protein thereof inserted between an N gene region and a P gene region in a measles virus genome.

2. The recombinant measles virus according to 1,
 in which the protein is a spike protein of SARS-COV-2 or a partial protein thereof.

3. The recombinant measles virus according to 1 or 2,
 in which the measles virus genome is an RNA consisting of a base sequence complementary to a base sequence set forth in SEQ ID NO: 1.

4. A genomic RNA of the recombinant measles virus according to any one of 1 to 3.

5. An RNA consisting of a base sequence complementary to a base sequence set forth in SEQ ID NO: 3.

6. A DNA including a gene encoding a protein of SARS-COV-2 inserted into a region ranging from a 1,686th base to a 1,694th base in a base sequence set forth in SEQ ID NO: 2.

7. A DNA including a gene encoding a protein of SARS-COV-2 or a partial protein thereof inserted into an Fse I recognition sequence located from a 1,686th base to a 1,694th base of a base sequence set forth in SEQ ID NO: 1.

8. A DNA consisting of a base sequence set forth in SEQ ID NO: 3.

9. A vector for producing a COVID-19 vaccine, the vector including the DNA according to any one of 6 to 8.

10. A plasmid vector including a DNA consisting of a base sequence set forth in SEQ ID NO: 1.

11. A method for producing a recombinant measles virus, the method including transfecting a vector for producing a COVID-19 vaccine including the DNA according to any one of 6 to 8 and an expression vector for an N protein, a P protein, and an L protein of a measles virus into a cell expressing an RNA polymerase capable of transcribing an RNA using the DNA as a template to produce a recombinant measles virus in the cell.

12. A pharmaceutical composition including:
 the recombinant measles virus according to any one of 1 to 3; and
 a pharmaceutically acceptable carrier.

13. The pharmaceutical composition according to 12, in which the pharmaceutical composition is used as a bivalent vaccine against measles and COVID-19.

14. A use of the recombinant measles virus according to any one of 1 to 3 as a vaccine against COVID-19.

15. A use of the recombinant measles virus according to any one of 1 to 3 for producing a vaccine against COVID-19.

16. A method for inducing an immune response against coronavirus SARS-COV-2, the method including:
 administering a pharmaceutical composition including the recombinant measles virus according to any one of 1 to 3 to a subject in need of prevention of COVID-19.

Advantageous Effects of Invention

The recombinant measles virus according to the present invention is useful as a vaccine against COVID-19.

In addition, the recombinant measles virus according to the present invention can be produced by a vector for producing a COVID-19 vaccine according to the present invention and the method for producing a recombinant measles virus using the vector.

DESCRIPTION OF EMBODIMENTS

Figure 1:
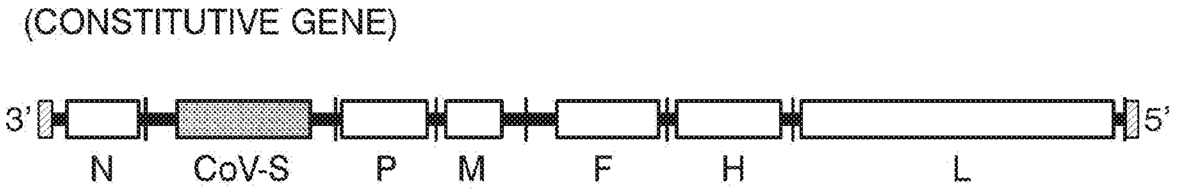
FIG. 1 is a view schematically showing the genomic structure of a recombinant measles virus (MV-CoVS) having a spike protein (CoV-S) gene of SARS-COV-2 in Example 1.

In the present invention and the present specification, the term "measles virus genome" means a genomic RNA capable of producing an infectious measles virus, the genomic RNA having no foreign gene encoding a protein. The measles virus genome may be either a genomic RNA of wild-type epidemic measles virus or a genomic RNA of an attenuated measles strain, or may be an RNA obtained by subjecting the genomic RNA to various genetic modification treatments other than insertion of a foreign gene encoding a protein.

In the present invention and the present specification, the term "recombinant measles virus" is an infectious virus which expresses a foreign protein. In the genomic RNA of the recombinant measles virus, a foreign structural gene encoding a protein is inserted into a region other than a gene region encoding a protein of measles virus.

In the recombinant measles virus according to the present invention, a gene encoding a protein of coronavirus SARS-COV-2 or a partial protein thereof is inserted between the N gene region and the P gene region in the measles virus genome. In a recombinant measles virus in which a protein of SARS-COV-2 or a partial protein thereof is inserted between the N gene region and the P gene region of the measles virus genome, the protein of SARS-COV-2 or a partial protein is expressed within the infected cell to induce immunity against these proteins. In addition, since the recombinant measles virus further maintains a function as a measles virus, it is also effective as a vaccine against measles.

The recombinant measles virus according to the present invention induces the production of an antibody against the protein of SARS-COV-2 or a partial protein thereof expressed in the infected cell. Therefore, the recombinant measles virus induces the production of an antibody against SARS-COV-2 and has a strong protective effect against COVID-19 and measles. Furthermore, similar to the live measles vaccine used in the related art, the recombinant measles virus can be expected to induce not only humoral immunity but also cellular immunity, and to confer immunity persistence for a long period of time called permanent immunity. In addition, the likelihood of ADE occurring through the administration of the recombinant measles virus is expected to be low. Similar to the live measles vaccines in the related art, the recombinant measles virus makes it possible to produce a pharmaceutical composition at a comparatively low cost and to make it into a freeze-dried preparation, whereby the problem of cold chain storage can also be solved.

For the production of the recombinant measles virus according to the present invention, for example, a reverse genetic system used for the reconstruction of a canine distemper virus or a measles virus described in Japanese Unexamined Patent Application, First Publication No. 2001-275684 or Japanese Unexamined Patent Application, First Publication No. 2010-115154 can be used. The measles virus belongs to a (−) strand RNA virus, and modification of the viral genome and introduction of a foreign gene can be performed using a widely used genetic modification technique for a cDNA of the measles virus genome. In the reverse genetic system, recombinant measles virus particles having infectivity are produced from a recombinant cDNA obtained by introducing a foreign gene into a cDNA of a genomic RNA of the measles virus. The genomic RNA of the produced recombinant measles virus is an RNA consisting of a base sequence complementary to the recombinant cDNA used for the production.

Recombinant cDNA

Specifically, for the cDNA of the measles virus genome, first, a gene encoding a protein of SARS-COV-2 or a partial protein thereof is incorporated between the N gene region and the P gene region to obtain a recombinant cDNA.

The measles virus genome used for production of the recombinant measles virus according to the present invention is not particularly limited as long as it is a genomic RNA of a measles virus capable of inducing a neutralizing antibody against wild-type epidemic measles virus. The measles virus may be, for example, a natural virus strain such as an HL strain and an ICB strain, or an attenuated strain such as an Edmonston strain and an AIC strain, or may be a genetically modified virus strain within a range not impairing induction for producing a neutralizing antibody against the measles virus.

As the recombinant measles virus according to the present invention, a recombinant measles virus having a protein of SARS-COV-2 or a partial protein thereof incorporated into a genomic RNA of an attenuated strain, or a genetically modified virus strain thereof is preferable from the viewpoint that it can be expected to have a higher protective effect against COVID-19 and higher safety.

Examples of the attenuated measles strain include a strain obtained by passaging an Edmonston wild-type strain to a measles non-susceptible animal-derived cell. The sequence identity of full-length genomic RNAs and the number of mismatched bases of various known attenuated strains are shown in Table 1 (Non-Patent Document 1).

TABLE 1

| Strain | Number of mismatched bases | Identity |
|---|---|---|
| Leningrad-4 | 36 | 99% |
| Edmonston B | 38 | 99% |
| Edmonston wt | 42 | 99% |
| Zagreb | 42 | 99% |
| Moraten | 44 | 99% |
| Schwarz | 44 | 99% |
| Changchun-47 | 47 | 99% |
| AIK-C | 48 | 99% |
| Shanghai-191 | 56 | 99% |
| CAM-70 | 75 | 99% |

The strain is affected by the characteristics of a recombinant measles virus thus obtained, depending on the type of attenuated strain used as a host. As the attenuated measles strain used as a host for constructing the recombinant measles virus according to the present invention, an attenuated measles strain having, as a genomic RNA, an RNA consisting of a base sequence complementary to a base sequence set forth in SEQ ID NO: 2 is preferable. The genomic RNA has 30 bases different from the full-length genomic RNA (GenBank Accession No.: Z66517) of the Edmonston B strain (Rubeovax).

As the cDNA of the measles virus genome used in constructing the recombinant measles virus according to the present invention, a DNA in which a restriction enzyme recognition sequence for inserting a foreign structural gene is arranged as appropriate between each of N, P, M, F, H, and L genes encoding proteins constituting the viruses. In particular, it is preferable to use a cDNA of a measles virus genome in which a restriction enzyme recognition sequence is positioned between the N gene region and the P gene region (which may be hereinafter referred to as a "modified cDNA").

The restriction enzyme recognition sequence inserted between the N gene region and the P gene region of the cDNA of the measles virus genome is not particularly limited as long as it is a restriction enzyme recognition sequence that can exist between the N gene region and the P gene region at only one site in the entire length of the cDNA. Specifically, for example, a recognition sequence such as Fse I can be used. The insertion of a restriction enzyme recognition sequence between any of the genes encoding proteins constituting a virus in the cDNA of the measles virus genome can be carried out by, for example, the methods described in Patent Document 1 and Patent Document 2.

As the modified cDNA used for constructing the recombinant measles virus according to the present invention, a DNA consisting of a base sequence in which a restriction enzyme recognition sequence is positioned between the N gene region and the P gene region in the base sequence set forth in SEQ ID NO: 2 is preferable, a DNA consisting of a base sequence in which an Fse I recognition sequence is inserted between the N gene region and the P gene region in the base sequence set forth in SEQ ID NO: 2 is more preferable, and a DNA consisting of the base sequence (GenBank Accession No.: MT409882) set forth in SEQ ID NO: 1 is still more preferable. Furthermore, the base sequence set forth in SEQ ID NO: 1 is a base sequence having an Fse I recognition sequence in the region ranging from the 1,686th base to the 1,694th base between the N gene region and the P gene region in the base sequence set forth in SEQ ID NO: 2.

The protein of SARS-COV-2 or a partial protein thereof may be a protein present in SARS-COV-2 or a partial protein thereof. The recombinant measles virus according to the present invention is preferably the spike protein of SARS-COV-2 or a partial protein thereof from the viewpoint that this can be expected to have a higher protective effect against COVID-19. The cDNA of a gene encoding the spike protein of SARS-COV-2 or a partial protein thereof can be obtained by an ordinary method based on a base sequence of a genomic RNA of SARS-COV-2 (NCBI Accession No.: NC_045512.2). Furthermore, the gene region encoding the spike protein of SARS-COV-2 is a region ranging from the 21,563rd base to the 25,384th base of the genomic RNA.

For example, by performing RT-PCR using a genomic RNA extracted from SARS-CoV-2 and a primer designed based on the base sequence information of the genomic RNA, the fragment of cDNA encoding the spike protein or a partial protein thereof can be synthesized. The primer can be designed using software generally used for designing a PCR primer. In a case where a fragment of the cDNA encoding the spike protein or a partial protein thereof is inserted into a modified cDNA in which a restriction enzyme recognition sequence is positioned between the N gene region and the P gene region, RT-PCR is performed using a primer in which the restriction enzyme recognition sequence is arranged at the 5' end. This makes it possible to obtain a DNA fragment in which the restriction enzyme recognition sequence is arranged at both ends of the cDNA encoding the spike protein or a partial protein thereof. Alternatively, a full-length DNA fragment of the cDNA encoding the spike protein or a partial protein thereof, or a DNA fragment in which restriction enzyme recognition sequences are arranged at both ends of the cDNA can also be produced by chemical synthesis.

A DNA fragment encoding a protein of SARS-COV-2 or a partial protein thereof is inserted between the N gene region and the P gene region in the cDNA of the measles virus genome to obtain a recombinant cDNA. In a case of using a restriction enzyme recognition sequence, both the DNA fragment of the modified cDNA in which the restriction enzyme recognition sequence is located between the N gene region and the P gene region, and the DNA fragment having the restriction enzyme recognition sequence arranged at both ends of the cDNA encoding the protein of SARS-COV-2 or a partial protein thereof are subjected to a restriction enzyme treatment, and then linked to each other by a ligation reaction, whereby a desired recombinant cDNA can be obtained.

The recombinant measles virus according to the present invention may undergo modifications such as insertion, deletion, or substitution of bases at any site in the genomic RNA as long as the preventive ability against COVID-19 and measles is maintained. For example, genes involved in RNA replication of some measles virus may be modified in order to inactivate genes involved in immunogenicity or to increase the transcription efficiency or the replication efficiency of RNAs. Specific examples of the modification include a modification of an intervening sequence and a modification of a leader portion.

In the recombinant measles virus according to the present invention, any other foreign gene may be inserted into any site in the genomic RNA as long as the preventive ability against COVID-19 and measles is maintained. Examples of other foreign genes to be inserted include genes encoding various proteins that induce pathogenicity in viruses, bacteria, and parasites which can be expressed in the host, genes encoding various cytokines, genes encoding various peptide hormones, and genes encoding antigen recognition sites in the antibody molecules. Examples of such genes include genes encoding various proteins, such as influenza virus, Mumps virus, HIV, dengue virus, diphtheria, and leishmania, or antigen recognition site genes of monoclonal antibodies against cancer-specific marker molecules.

Vector for Producing COVID-19 Vaccine

A vector including a DNA in which the recombinant cDNA is connected downstream of a specific promoter can be used for production of the recombinant measles virus according to the present invention. The recombinant measles virus according to the present invention is effective as a vaccine against COVID-19, and the vector is used as a vector for producing a COVID-19 vaccine. The vector for producing a COVID-19 vaccine is preferably a plasmid vector, but may be a linear DNA vector.

For example, a vector for producing a COVID-19 vaccine can be produced by connecting a DNA fragment including the promoter sequence to a DNA fragment including the recombinant cDNA such that the recombinant cDNA is connected downstream of the promoter sequence, and incorporating the linked construct into a plasmid. The linking between DNA fragments and the insertion into a plasmid can be performed by a genetic recombination technique.

In the vector for producing a COVID-19 vaccine, the promoter upstream of the recombinant cDNA can be appropriately selected from promoters recognized by known DNA-dependent RNA polymerases, and then used. Examples of the promoter include a T7 promoter, an SP6 promoter, and a T3 promoter.

Specifically, as the vector for producing a COVID-19 vaccine, a plasmid vector incorporated with a DNA having a gene encoding the protein of SARS-COV-2 is inserted into a region ranging from the 1,686th base to the 1,694th base in the base sequence set forth in SEQ ID NO: 2, a DNA in which a gene encoding the protein of SARS-COV-2 is inserted into an Fse I recognition site located at the 1,686th base to the 1,694th base of the base sequence set forth in SEQ ID NO: 1, or a DNA fragment in which a promoter is linked upstream of any DNA of DNAs consisting of the base sequence set forth in SEQ ID NO: 3 is preferable, and a plasmid vector incorporated with a DNA fragment in which a T7 promoter, a T3 promoter, or an SP6 promoter is linked upstream of a DNA consisting of the base sequence set forth in SEQ ID NO: 3 is more preferable.

Gene Recombinant Vector

The vector for producing a COVID-19 vaccine can be more easily produced by using a plasmid vector including a modified cDNA in which a restriction enzyme recognition sequence is arranged between the N gene region and the P gene region. Among the plasmid vectors, in particular, a plasmid vector in which a modified cDNA having a restriction enzyme recognition sequence arranged between the N gene region and the P gene region is connected downstream of a promoter is useful as a gene recombinant vector for producing a bivalent vaccine against measles and other diseases.

The insertion of a modified cDNA or a promoter fragment into a plasmid vector can be performed by a genetic modification technique such as a ligation reaction. Furthermore, the promoter connected upstream of the modified cDNA can be appropriately selected from promoters recognized by known DNA-dependent RNA polymerases such as a T7 promoter, a T3 promoter, and a SP6 promoter, and then used.

As the modified cDNA to be inserted into the genetic recombinant vector, a DNA consisting of a base sequence in which a restriction enzyme recognition sequence is arranged in a region ranging from the 1,686th base to the 1,694th base in the base sequence set forth in SEQ ID NO: 2 is preferable, and a DNA consisting of the base sequence set forth in SEQ ID NO: 1 is more preferable. A plasmid vector including a base sequence in which the base sequence set forth in SEQ ID NO: 1 is connected downstream of a promoter sequence is very useful as a genetic recombinant vector.

For example, for a plasmid vector including a base sequence in which the base sequence set forth in SEQ ID NO: 1 is connected downstream of a promoter sequence, a vector for producing a COVID-19 vaccine can be produced by incorporating a DNA fragment having a base sequence in which an Fse I recognition sequence is arranged at both ends of a gene encoding a spike protein or a partial protein thereof into an Fse I recognition sequence in the base sequence set forth in SEQ ID NO: 1 by genetic manipulation. In addition, it is possible to produce a vector that enables the production of a recombinant measles virus effective as a vaccine against both measles and other diseases by incorporating a DNA fragment including a gene encoding a protein that induces an immune response effective for preventing COVID-19 and diseases other than measles, instead of a DNA fragment including a gene encoding the spike protein or a partial protein thereof.

Method for Producing Recombinant Measles Virus

The vector for producing a COVID-19 vaccine is transfected into a cell which carries an RNA polymerase capable of transcribing an RNA using a cDNA of the measles virus genome incorporated into the vector as a template, and any in a group of enzymes required for the transcriptional replication of the measles virus. Inside the cell, a genomic RNA of the recombinant measles virus is synthesized using the cDNA of the measles virus genome incorporated into the vector as a template by the polymerase. Inside the cell, a recombinant measles virus is produced by the genomic RNA and the group of enzymes required for the transcriptional replication of the measles virus. That is, the genomic RNA of the produced recombinant measles virus is an RNA consisting of a base sequence complementary to the recombinant cDNA used for production.

Examples of the RNA polymerase for transcribing an RNA using cDNA of the measles virus genome as a template include a DNA-dependent RNA polymerase that acts on a promoter connected upstream of the cDNA of the measles virus genome incorporated into the vector for producing a COVID-19 vaccine. In a case where the promoter connected upstream of the cDNA of the measles virus genome is a T7 promoter, for example, a T7 RNA polymerase can be used as the DNA-dependent RNA polymerase. Examples of the cell expressing the RNA polymerase include a cell infected in advance with a recombinant vaccinia virus that expresses the T7 RNA polymerase, and a T7 RNA polymerase constant expression strain in which the T7 RNA polymerase gene is incorporated into a chromosome of a cultured cell.

Examples of the group of enzymes required for the transcriptional replication of the measles virus include the N protein, the P protein, and the L protein of the measles virus. Examples of the cell carrying all the group of enzymes required for the transcriptional replication of the measles virus include a cell transfected with all of an expression vector incorporated with a gene encoding the N protein (an expression vector for the N protein), an expression vector incorporated with a gene encoding the P protein (an expression vector for the P protein), and an expression vector incorporated with a gene encoding the L protein (an expression vector for the L protein).

For example, any of the vector for producing a COVID-19 vaccine, the expression vector for the N protein, the expression vector for the P protein, and the expression vector for the L protein are transfected into the cultured cell infected in advance with the recombinant vaccinia virus that expresses a T7 RNA polymerase are transfected together. Inside the transfected cell, a recombinant measles virus carrying a genome with an RNA consisting of a base sequence complementary to the recombinant cDNA used for production is constructed.

The produced recombinant measles virus can be used as a vaccine against COVID-19. That is, the produced recombinant measles virus proliferates in the infected cells, and further, the spike protein of SARS-COV-2 or a partial protein thereof is expressed to induce the production of an antibody against the protein. Therefore, the recombinant measles virus functions as a vaccine against COVID-19 as well as a vaccine against measles.

Pharmaceutical Composition

A vaccine against COVID-19 can be produced by using the recombinant measles virus according to the present invention. For example, a pharmaceutical composition including the recombinant measles virus and the pharmaceutically acceptable carrier in which the pharmaceutical composition is useful as a bivalent vaccine against measles and COVID-19 can be produced by appropriately mixing the recombinant measles virus according to the present invention and a pharmaceutically acceptable carrier. The production of the pharmaceutical composition including the recombinant measles virus and the pharmaceutically acceptable carrier can be carried out using appropriate additives as necessary by a method which is commonly used in the field of production of pharmaceuticals.

The pharmaceutically acceptable carrier is a diluent, an excipient, a binder, a solvent, or the like which does not cause a harmful physiological reaction to an administration subject and does not result in a harmful interaction with other ingredients such as pharmacologically active ingredients. As the carrier, specifically, water, physiological saline, various buffer solutions, or the like is used. In addition, examples of the additives that can be used include an adjuvant, a diluent, an excipient, a binder, a stabilizer, an isotonic agent, a buffering agent, a solubilizing agent, a suspending agent, a preservative, an antifreeze agent, a cryoprotective agent, a freeze-drying protective agent, and a bactericidal agent.

An adjuvant commonly used in the field of pharmaceuticals can be used as the adjuvant for enhancing immunogenicity. Specific examples thereof include microbial cells such as BCG and *Propionibacterium acnes*, cell walls, microbial cell components such as trehalose dimycolate (TDM), synthetic compounds such as lipopolysaccharides (LPS) or lipid A fractions of which are endotoxins of Gram-negative bacteria, β-glucan, N-acetylmuramyl dipeptide (MDP) pestatin, or levamiazole, proteins derived from biological components such as thymus hormones, thymus factors, and tuftsin, peptide substances, Freund's incomplete adjuvant, and Freund's complete adjuvant.

The dosage form of the vaccine may be any one of a liquid form, a frozen product, and a freeze-dried product. A culture solution obtained by culturing in an appropriate medium, cultured cells, and the like is collected, an additive such as a stabilizer is added thereto, and the mixture is dispensed into a small bottle, an ampoule, or the like, and then sealed, whereby a liquid vaccine can be produced. After being dispensed, the vaccine that is frozen by gradually lowering the temperature is a frozen vaccine, to which an antifreeze agent or a freeze-protective agent is added. In a case where the dispensed container is frozen in a freeze dryer and then vacuum-dried, and the container is sealed as is or by being filled with nitrogen gas, it is possible to obtain a freeze-dried vaccine. The liquid vaccine is used as is or after being diluted with physiological saline or the like. For the frozen vaccine and the dried vaccine, a dissolution solution for dissolving the vaccine at the time of use is used. The solutions for dissolution are various buffer solutions or physiological saline.

An immune response against SARS-COV-2 can be induced in the subject by administering an effective amount of a pharmaceutical composition including the recombinant measles virus according to the present invention to a subject as a vaccine. The administration of the vaccine can be performed by subcutaneous administration, intramuscular administration, intravenous administration, or the like. The dosage varies depending on age, body weight, sex, administration method, or the like of the subject and is not particularly limited, but is preferably in a range of usually $10^4$ to $10^7$ $TCID_{50}$ per dose, and particularly preferably at least $10^4$ $TCID_{50}$. The administration is preferably performed in the same manner as that for the measles vaccine.

In addition, after various animals including humans are infected with the recombinant measles virus according to the present invention, antisera and the like can be obtained from body fluids collected from animals for use in treatment or diagnosis.

EXAMPLES

Next, the present invention will be more specifically described with reference to Examples and the like, but the present invention is not limited to the Examples.

Example 1

A recombinant measles virus (MV-CoVS) having a spike protein (CoV-S) gene of SARS-COV-2 was constructed.

Preparation of Plasmid pMV-CoVS Including cDNA of Genomic RNA of Recombinant Measles Virus Having CoV-S Gene First, an RNA was extracted from a measles virus that is an attenuated measles strain with a genomic RNA in which the RNA consists of a base sequence complementary to the base sequence set forth in SEQ ID NO: 2, and RT-PCR was performed using the obtained RNA as a template. The full-length genomic RNA was divided into several partial regions and subjected to RT-PCR, and the obtained amplified fragments were linked to obtain a plasmid pMV-Ed in which a DNA fragment consisting of the base sequence set forth in SEQ ID NO: 1 was linked downstream of the T7 promoter in the plasmid pMDB1.

The cDNA of the CoV-S gene was obtained by RT-PCR using the entire RNA extracted from the SARS-COV-2-infected Vero cell. PCR was carried out using the obtained cDNA as a template and using a primer set having an Fse I recognition sequence at the 5' end, thereby obtaining a DNA fragment encoding the spike protein having Fse I recognition sequences at both ends (CoV-S fragment: SEQ ID NO: 4).

The plasmid pMV-Ed and the CoV-S fragment were digested with Fse I, and the two were linked by ligation. The product was inserted into the Fse I recognition site of pMV-Ed to obtain a plasmid pMV-CoVS having a cDNA having the genomic structure shown in FIG. 1.

Reconstitution of MV-CoVS

For the replication of the measles virus, an N protein expression vector pGEM-NP in which the N protein gene of the measles virus was inserted into a plasmid pGEM, a P protein expression vector pGEM-P in which the P protein gene of the measles virus was inserted into pGEM, and L protein expression vectors pGEM-L and pMV-CoVS in which the L protein gene of the measles virus was inserted into pGEM were used. 2 μg of pGEM-NP, 2 μg of pGEM-P, 0.2 μg of pGEM-L, and 2 μg of pMV-CoVS were added into a 1.5 mL sampling tube containing 1 mL of Opti-MEM (manufactured by Thermo Fisher Scientific, Inc.) to prepare a nucleic acid solution. 1 mL of Opti-MEM was collected into another sampling tube, a transfection reagent "Lipofectamin LTX" (manufactured by Thermo Fisher Scientific, Inc.) was added thereto and mixed, and then the mixture was left to stand at room temperature for 5 minutes in this state. Thereafter, the transfection reagent solution was mixed with the nucleic acid solution, and the mixture was further allowed to stand at room temperature for 15 minutes or longer and used as a plasmid solution.

Cultured cell strain BHK-T7 cells which had been subjected to a common trypsin treatment were added into each well of a 6-well plate at a density of $5\times10^5$ cells per well along with 2 mL of a culture medium (a DMEM medium including 2% fetal bovine serum), and the plate was cultured for 6 hours under conditions of 5% $CO_2$ and 37° C. Thereafter, 200 μL of the plasmid solution was added dropwise to each well.

The cells in the 6-well plate were cultured for 2 days under the conditions of 5% $CO_2$ and 37° C. After removing the culture medium on the second day, the Vero cells suspended in VP-SFM (manufactured by Gibco BRL/Life Technologies) were seeded at a density of $5\times10^5$ cells per well, and the cells were overlaid on the BHK-T7 cells. In a case where the plate was further cultured under the conditions of 5% $CO_2$ and 37° C., a cytopathic effect (CPE) was observed on the Vero cells. The CPE thereof indicates that MV-CoVS increased in the Vero cells infected with the recombinant measles virus MV-CoVS reconstituted in BHK-T7 cells.

RT-PCR was performed using, as a template, the RNA extracted from the Vero cells in which CPE was observed, and sequence analysis of the obtained PCR fragment was performed to confirm that the recombinant measles virus MV-CoVS was reconstructed in the Vero cells.

Furthermore, the Vero cells in which CPE was observed were subjected to fluorescent immunostaining using an antibody against CoV-S(anti-CoV-S antibody) as a primary antibody. First, the Vero cells were infected with the recombinant measles virus MV-CoVS, and after 48 hours, the cells were fixed with 4% paraformaldehyde and permeabilized with 0.2% Triton X-100. Next, a 1,000-fold diluted anti-CoV-S antibody (mouse serum) was added thereto and allowed to react at room temperature for 1 hour. After removing the anti-CoV-S antibody and washing the cells three times with PBS, an Alexa 488-labeled anti-mouse IgG antibody was diluted 500-fold and added thereto, and incubation was performed at room temperature for 30 minutes to cause a reaction. After removing the Alexa488-labeled anti-mouse IgG antibody and washing the cells five times with PBS, the MV-CoVS-infected Vero cells were then observed using a confocal laser scanning microscope.

Figure 2:
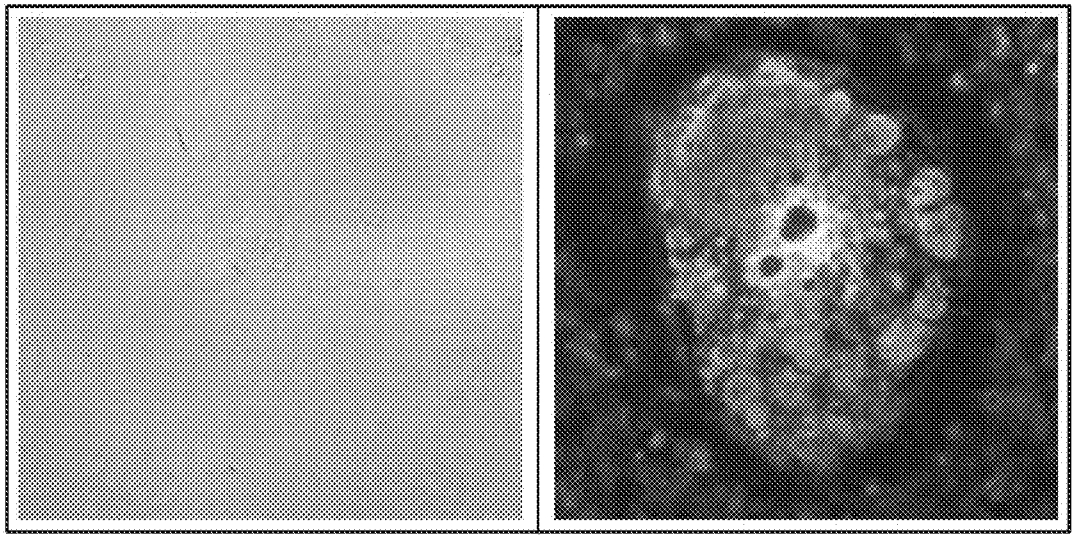
FIG. 2 shows a transmission image of a Vero cell in which CPE was observed (left figure) and an image obtained by fluorescent immunostaining of a spike protein of SARS-CoV-2 (right figure) in Example 1.

A transmission image of MV-CoVS-infected Vero cells (left figure) and an image obtained by fluorescent immunostaining of a spike protein of SARS-COV-2 (right figure) are shown in FIG. 2. As shown in FIG. 2, Alexa488 fluorescence was not observed in the Vero cells not infected with MV-CoVS, but Alexa488 fluorescence was observed in the MV-CoVS-infected Vero cells. From these results, it was confirmed that the CoV-S protein was expressed in the Vero cells infected with the recombinant measles virus MV-CoVS, that is, that a recombinant measles virus expressing the CoV-S protein could be constructed.

Figure 3:
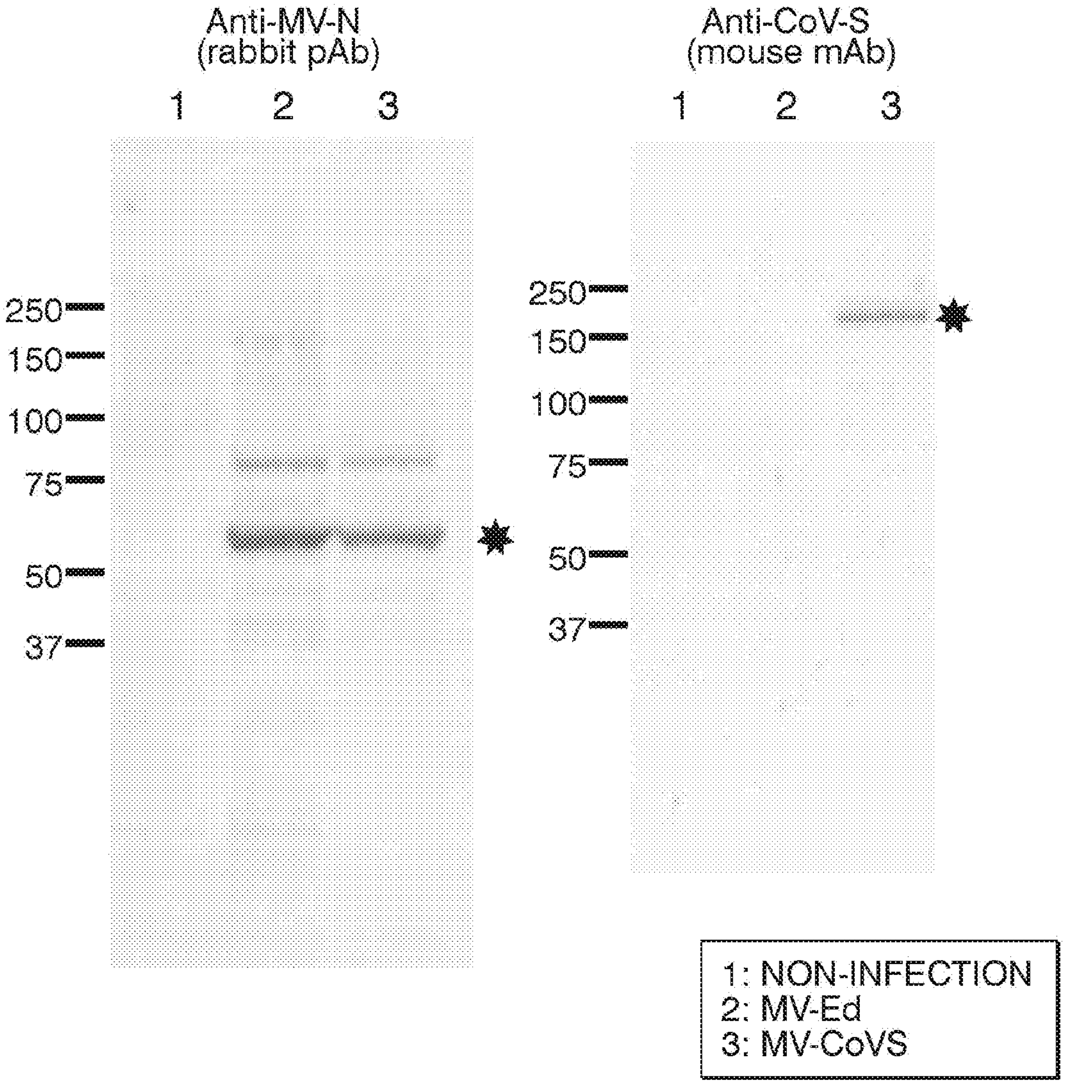
FIG. 3 is a view showing the results of Western blotting analysis using an antibody (anti-MV-N antibody) recognizing an N protein of a measles virus and an anti-CoV-S antibody with regard to a Vero cell (non-infected cell) not infected with a measles virus, a Vero cell (MV-Ed cell) infected with a measles virus MV-Ed, and a Vero cell (MV-CoVS cell) infected with a measles virus MV-CoVS in Example 1.

A Vero cell not infected with a measles virus (non-infected cell), a Vero cell infected with a measles virus MV-Ed (MV-Ed cell), and a Vero cell infected with a measles virus MV-CoVS (MV-CoVS cell) were subjected to Western blotting analysis using an antibody (anti-MV-N antibody) recognizing the N protein of the measles virus and an anti-CoV-S antibody. The results of Western blotting using the anti-MV-N antibody and the anti-rabbit IgG antibody are shown in FIG. 3 (left), and the results of Western blotting using the anti-CoV-S antibody and the anti-mouse IgG antibody are shown in FIG. 3 (right). A band of the MV-N protein was confirmed in both the MV-Ed cells and the MV-CoVS cells (FIG. 3 (left), asterisk), but a band of the CoV-S protein was confirmed only in the MV-CoVS cells (FIG. 3 (right), asterisk).

Furthermore, a hamster was inoculated with the measles virus MV-CoVS to investigate whether antibody production was induced. Specifically, the hamster was intraperitoneally (IP) inoculated twice with the measles virus MV-CoVS, and the blood was collected over time to measure the titer of the anti-CoV-S antibody in the serum. The second virus inoculation was performed at 5 weeks (on the 35th day) from the first inoculation. As a control, a hamster was inoculated with the measles virus MV-Ed in the same manner. The titer of the anti-CoV-S antibody in the serum was measured over time. The titer of the anti-CoV-S antibody in the serum was measured by an ELISA method using the serum.

Figure 4:
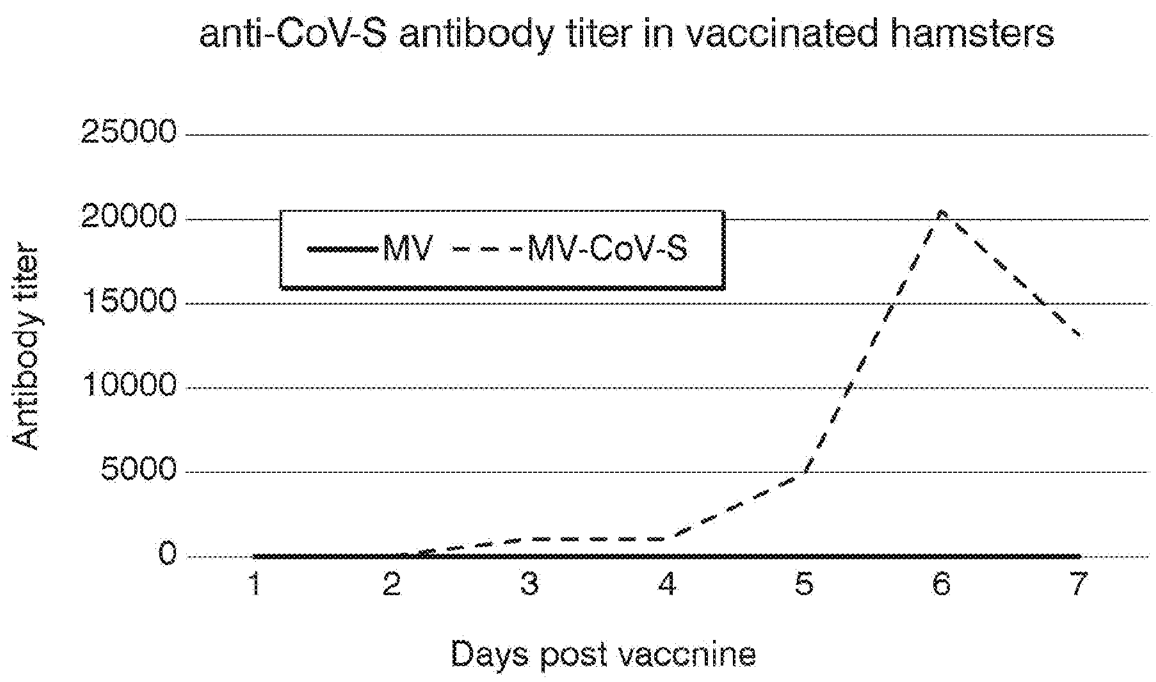
FIG. 4 is a view showing the measurement results for a titer of an anti-CoV-S antibody in the serum over time by inoculating hamsters twice with each of the measles virus MV-CoVS and the measles virus MV-Ed in Example 1.

The results of measurement of the titer of the anti-CoV-S antibody in the serum over time from the first vaccination (day 0) are shown in FIG. 4. The production of the anti-CoV-S antibody in the serum was not observed in the hamster inoculated with the measles virus MV-Ed. In contrast, in the hamster inoculated twice with the measles virus MV-CoVS, the titer of the anti-CoV-S antibody in the serum was increased and the production of the anti-CoV-S antibody was induced by vaccinating twice. As shown in these results, the measles virus MV-CoVS has an immunity induction ability and is a useful candidate for a vaccine against COVID-19.

The invention claimed is:

1. An isolated recombinant measles virus, comprising:

a measles virus genome, and a gene encoding a protein of coronavirus SARS-COV-2 inserted between the N gene region and the P gene region in the measles virus genome, wherein the measles virus genome comprises a base sequence complementary to the full length of the base sequence of SEQ ID NO: 1.

2. The recombinant measles virus according to claim 1, wherein the protein is a spike protein of SARS-COV-2 or an immunogenic fragment thereof.

3. An isolated genomic RNA comprising the full-length base sequence of the genome of the recombinant measles virus according to claim 1.

4. An isolated RNA comprising a base sequence complementary to the full length of the base sequence of SEQ ID NO: 3, or an isolated DNA comprising the full length of the base sequence of SEQ ID NO: 3, or an isolated plasmid vector comprising a DNA comprising the full length of the base sequence of SEQ ID NO: 1.

5. An isolated DNA comprising:

1) the base sequence of SEQ ID NO: 2 except for the region ranging from the 1,686th base to the 1,694th base and a gene encoding a protein of SARS-COV-2 inserted into the region ranging from the 1,686th base to the 1,694th base in the base sequence of SEQ ID NO: 2, or 2) the base sequence of SEQ ID NO: 1.

6. An isolated vector for producing a COVID-19 vaccine, the vector comprising:

the DNA according to claim 5.

7. A method for producing a recombinant measles virus, the method comprising:

transfecting a vector for producing a COVID-19 vaccine including the DNA according to claim 5 and an expression vector for an N protein, a P protein, and an L protein of a measles virus into a cell expressing an RNA polymerase capable of transcribing an RNA using the DNA as a template to produce a recombinant measles virus in the cell.

8. A pharmaceutical composition comprising:

the recombinant measles virus according to claim 1; and a pharmaceutically acceptable carrier.

9. The pharmaceutical composition according to claim 8, wherein the pharmaceutical composition is used as a bivalent vaccine against measles and COVID-19.

10. A method for inducing an immune response against coronavirus SARS-COV-2, the method comprising:

administering a pharmaceutical composition including the recombinant measles virus according to claim 1 to a subject in need thereof.

* * * * *